US012685849B2

(12) United States Patent
Simopoulos

(10) Patent No.: US 12,685,849 B2
(45) Date of Patent: Jul. 21, 2026

(54) METHOD AND SYSTEM FOR ABSCESS DRAINAGE

(71) Applicant: Christopher Simopoulos, Loomis, CA (US)

(72) Inventor: Christopher Simopoulos, Loomis, CA (US)

(*) Notice: Subject to any disclaimer, the term of this patent is extended or adjusted under 35 U.S.C. 154(b) by 421 days.

(21) Appl. No.: 18/089,400

(22) Filed: Dec. 27, 2022

(65) Prior Publication Data

US 2023/0201543 A1 Jun. 29, 2023

Related U.S. Application Data

(60) Provisional application No. 63/300,910, filed on Jan. 19, 2022, provisional application No. 63/294,035, filed on Dec. 27, 2021.

(51) Int. Cl.
| | |
|---|---|
| *A61M 27/00* | (2006.01) |
| *A61B 17/32* | (2006.01) |
| *A61B 17/3211* | (2006.01) |
| *A61M 1/00* | (2006.01) |

(52) U.S. Cl.
CPC ......... *A61M 27/00* (2013.01); *A61B 17/3211* (2013.01); *A61M 1/84* (2021.05); *A61B 2017/320052* (2013.01)

(58) Field of Classification Search
CPC ............ A61M 25/065; A61M 25/0662; A61M 25/06; A61M 25/01; A61B 17/3415; A61B 17/3421; A61B 17/3401; A61B 17/32093; A61B 17/34; A61B 17/321; A61B 17/3417; A61B 2017/32005
See application file for complete search history.

(56) References Cited

U.S. PATENT DOCUMENTS

| | | | | |
|---|---|---|---|---|
| 3,204,634 | A * | 9/1965 | Koehn | A61L 29/085 |
| | | | | D24/112 |
| 3,469,580 | A * | 9/1969 | Huddy | A61M 5/3287 |
| | | | | 604/158 |
| 3,982,546 | A * | 9/1976 | Friend | A61M 1/71 |
| | | | | 604/173 |
| 5,472,435 | A * | 12/1995 | Sutton | A61M 27/00 |
| | | | | 604/540 |
| 6,589,212 | B1 * | 7/2003 | Navis | A61M 25/0017 |
| | | | | 604/164.01 |
| 2006/0206096 | A1 * | 9/2006 | Accisano | A61M 25/0074 |
| | | | | 604/540 |
| 2009/0163770 | A1 * | 6/2009 | Torrie | A61B 17/3421 |
| | | | | 600/114 |
| 2020/0316345 | A1 * | 10/2020 | Matthews | A61B 17/3401 |
| 2021/0038255 | A1 * | 2/2021 | Mei-Dan | A61B 17/3417 |

* cited by examiner

*Primary Examiner* — Elizabeth Houston
*Assistant Examiner* — Serenity A Miller
(74) *Attorney, Agent, or Firm* — Sheridan Ross P.C.

(57) ABSTRACT

The present disclosure is directed to methods and devices for fluid drainage from an abscess of a patient.

18 Claims, 27 Drawing Sheets

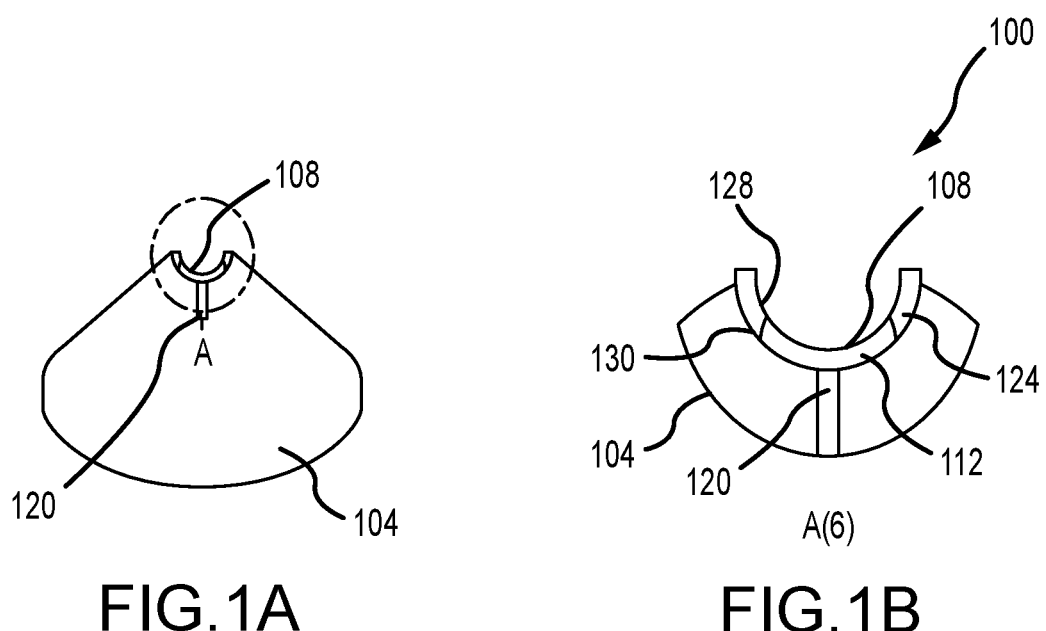
FIG.1A          FIG.1B
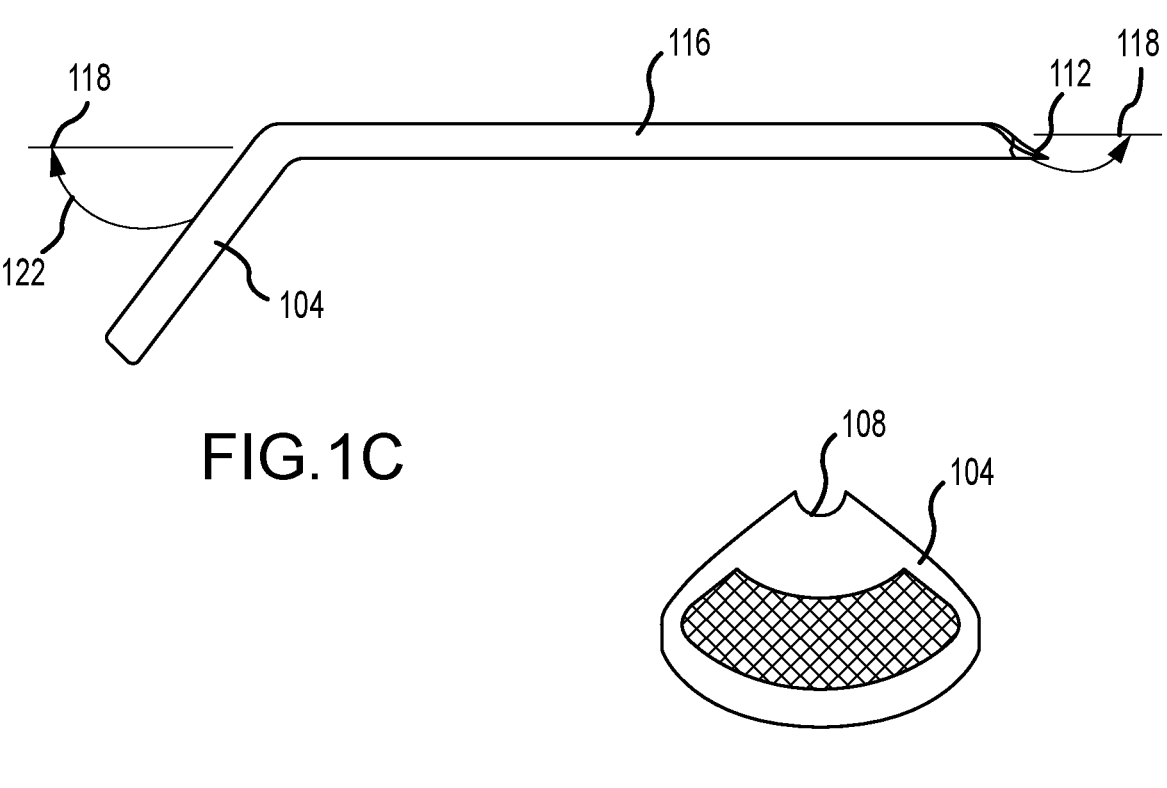
FIG.1C
FIG.1D

METHOD AND SYSTEM FOR ABSCESS DRAINAGE

CROSS-REFERENCE TO RELATED APPLICATIONS

The present application claims the benefit of and priority, under 35 U.S.C. § 119(e), to U.S. Provisional Application Ser. No. 63/294,035, filed on Dec. 27, 2021; and 63/300,910, filed on Jan. 19, 2022; each of which is entitled "Method and System for Abscess Drainage," the entire disclosures of which are hereby incorporated herein by reference, in its entirety, for all that each teaches and for all purposes.

FIELD

The disclosure relates generally to surgical tools and techniques and particularly to surgical and radiological tools and techniques for abscess drainage.

BACKGROUND

An abscess can develop under the skin or within a body, in an organ, or in the spaces between organs. It typically is a collection of pus that has built up within the tissue of the body to prevent the spread of an infectious material to other parts of the body. Abscesses are commonly caused by bacterial infection, parasites, or foreign substances. Perianal abscesses can be caused by inflammatory bowel disease or diabetes. Incisional abscesses develop as a complication secondary to a surgical incision.

The standard treatment for an uncomplicated skin or soft tissue abscess is the act of opening and draining. In the Seldinger technique, a needle is advanced into the abscess or fluid collection and its position confirmed with a computed tomography scan (CT scan). A guide wire is passed through the needle and into the abscess. When in the desired position, the needle is removed leaving the guide wire in place. The tract is then dilated with blunt plastic dialators (e.g., successively by 6, 8, and 10 French sized dilators) over the guide wire. The catheter is guided by the wire into the abscess, and, when the catheter is properly positioned, the wire is removed. The catheter is then locked in position and drainage until abscess drainage is completed.

The Seldinger technique has a number of drawbacks. It can cause substantial patient pain with each dilater, wire kinking with each dilator, loss of wire access to the abscess, and pus spillage into the peritoneal cavity with each tract dilation. The technique can be time intensive, typically requiring an hour or more. The technique can require an extra set of hands to run the dilators and catheter and avoid wire kinking or loss of wire access. After wire placement and needle removal, the position of the wire and catheter cannot be tracked by a CT scan, until the catheter is permanently placed in the abscess.

SUMMARY

These and other needs are addressed by the various embodiments and configurations of the present disclosure.

A first embodiment of the disclosure is directed to a scalpel that can include:
- a cutting tip;
- a handle; and
- an elongated body joining the cutting tip and the angled handle.

The elongated body includes a guide channel to receive and guide a catheter along a length of the guide channel. The handle is spatially offset from a longitudinal axis of the elongated body to enable movement of the scalpel without user interference.

The elongated body can include a composite material. The composite material can include a metal core extending substantially an entire length of the elongated body and a resin body positioned on either side of the metal core. The composite material can enable enhanced CT scanning location of the scalpel within body tissue and therefore improved intratissue guidance of the scalpel by a physician.

The guide channel can have a variety of profiles perpendicular to the longitudinal axis of the elongated body with a rounded cross-sectional profile being common.

A second embodiment of the disclosure is directed to a catheter assembly that can include:
- a catheter body that includes an aspiration port and a plurality of drainage ports, the aspiration port being in a distal portion of the catheter body (e.g., near the catheter tip) and the plurality of draining ports being proximal to the aspiration port;
- an inner stylet within the catheter body and extending a substantial length of the catheter body; and
- an outer stylet within the catheter body and extending a substantial length of the catheter body.

The inner and outer stylets move independently of each other to enable selective opening and closing of the aspiration port and drainage ports.

The catheter assembly can operate in different operational modes including:
- in a first operational mode, the inner and outer stylets are positioned simultaneously in the catheter body and block fluid drainage through the aspiration and drainage ports;
- in a second operational mode, the inner stylet is removed from the catheter body while the outer stylet remains in the catheter body, thereby forming a first lumen in a volume previously occupied by the inner stylet and enabling fluid drainage from the aspiration port along the first lumen while blocking fluid drainage through the plurality of drainage ports; and
- in a third operational mode, both the inner stylets and outer stylets are removed from the catheter body, thereby forming a second lumen in a volume previously occupied by the inner and outer stylets and enabling fluid drainage from the aspiration port and the drainage ports along the second lumen.

A third embodiment of the present disclosure is directed to a catheter assembly, that can include:
- a catheter body comprising a plurality of drainage ports;
- an inner stylet within the catheter body and extending a substantial length of the catheter body; and
- an outer stylet within the catheter body and extending a substantial length of the catheter body. The inner and outer stylets move independently of each other, and the outer stylus comprises a concave draining channel to receive and direct abscess fluid to an output of the catheter assembly.

The catheter assembly can have a number of benefits. The use of independently movable inner and outer stylets can enable location of the catheter tip relative to a fluid-containing structure, such as an abscess, by enabling the user to observe fluid drainage through the aspiration port and a first lumen formed by removal of the inner stylet. The outer stylet can have a concave profile perpendicular to a longitudinal axis of the catheter to direct drainage fluid along the first lumen and prevent unintended fluid leakage into body tissue via the outer stylet blocked drainage ports. When the catheter assembly is in the fluid-containing structure, the outer stylet can be removed to enable fluid drainage not only through the aspiration port but also through the drainage ports for relatively rapid fluid discharge from the structure.

A fourth embodiment of the present disclosure is directed to a treatment method that can include the steps:

advancing a needle through tissue of a patient until a point of the needle is in a first spatial position;

aligning a guide channel of a slotted scalpel with a cannula of the needle;

advancing a cutting tip of the slotted scalpel along the cannula and into the tissue of the patient;

when the cutting tip of the slotted scalpel is in a second spatial position within the tissue of the patient, removing the needle from the guide channel;

aligning a catheter with the guide channel of the slotted scalpel;

advancing a cutting tip of the catheter along the guide channel and into the tissue of the patient;

when the cutting tip of the catheter is in a third spatial position within the tissue of the patient, opening an aspiration port of the catheter to enable fluid drainage through the catheter while maintaining drainage ports of the catheter in closed positions blocking fluid drainage;

further advancing the catheter to a fourth spatial position within the tissue of the patient; and when the cutting tip of the catheter is in the fourth spatial position within the tissue of the patient, opening the drainage ports of the catheter to enable fluid drainage through the drainage ports.

The present disclosure can provide a number of advantages depending on the particular configuration. Unlike the Seldinger method, the CT scanner's ability to locate the scalpel can enable the physician user to easily and more accurately position the scalpel and therefore the catheter in less time and with less patient discomfort and increased patient safety. The aspiration port, in particular, can confirm the spatial location of the catheter assembly relative to the fluid-containing tissue structure. By using a needle and slotted scalpel, it can avoid the use of guide wire access to the abscess and the problems associated with guide wires, such as requiring an extra set of hands to run the dilators and catheter so as to avoid wire kinking or loss of wire access. It can therefore reduce patient pain by avoiding the use of dilaters and potential wire kinking with each dilator. By using independently movable inner and outer stylets in the catheter assembly, it can reduce, or eliminate altogether, puss spillage into the peritoneal cavity with each tract dilation. It can significantly reduce the amount of time required for abscess drainage, typically requiring only one-third of the time normally required by the Seldinger technique.

These and other advantages will be apparent from this disclosure.

The phrases "at least one", "one or more", "or", and "and/or" are open-ended expressions that are both conjunctive and disjunctive in operation. For example, each of the expressions "at least one of A, B and C", "at least one of A, B, or C", "one or more of A, B, and C", "one or more of A, B, or C", "A, B, and/or C", and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "cannula" refers to a tube that can be inserted into the body, often for the delivery or removal of fluid or for the gathering of samples. In simple terms, a cannula can surround the inner or outer surfaces of a trocar needle thus extending the effective needle length by at least half the length of the original needle. Its size mainly ranges from 14 to 24 gauge. Different-sized cannula have different colors as coded.

The term "catheter" refers to a thin tube made from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications. The process of inserting a catheter is "catheterization". In most uses, a catheter is a thin, flexible tube ("soft" catheter) though catheters are available in varying levels of stiffness depending on the application. A catheter left inside the body, either temporarily or permanently, may be referred to as an "indwelling catheter" (for example, a peripherally inserted central catheter). A permanently inserted catheter may be referred to as a "permcath" (originally a trademark). Catheters can be inserted into a body cavity, duct, or vessel, brain, skin or adipose tissue. Functionally, they allow drainage, administration of fluids or gases, access by surgical instruments, and also perform a wide variety of other tasks depending on the type of catheter.

The term "CT scan" refers to a computed tomography scan (formerly known as computed axial tomography or CAT scan) and is a medical imaging used in radiology to obtain detailed internal images of the body noninvasively for diagnostic purposes or forming images of non-living objects. CT scanners use a rotating X-ray and a row of detectors placed in the gantry to measure X-ray attenuations by different tissues inside the body. The multiple X-ray measurements taken from different angles are then processed on a computer using reconstruction algorithms to produce tomographic (cross-sectional) images (virtual "slices") of a body.

A "hypodermic needle" refers to a very thin, hollow tube with a sharp tip that is used to puncture the skin of a patient, such as for injection of substances into the body.

The term "means" as used herein shall be given its broadest possible interpretation in accordance with 35 U.S.C., Section(s) 112(f) and/or 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "scalpel" or lancet or bistoury refers to small and extremely sharp bladed instrument used for surgery. Surgical scalpels consist of two parts, a blade and a handle. The handles are often reusable, with the blades being replaceable. In medical applications, each blade is only used once (sometimes just for a single, small cut). Scalpel blades are usually made of hardened and tempered steel, stainless steel, or high-carbon steel; in addition, titanium, ceramic, diamond and even obsidian knives are not uncommon. A surgeon typically grasps the scalpel handle in a palmar grip or pencil grip for grip stability and precision.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

The preceding is a simplified summary of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various embodiments of the disclosure, as illustrated by the drawings referenced below.

FIG. 1A is a front view of a scalpel according to an embodiment of the present disclosure.

FIG. 1B is an exploded view of the front of the scalpel of FIG. 1A.

FIG. 1C is a side view of the scalpel of FIG. 1A.

FIG. 1D is an end view of the scalpel of FIG. 1A.

DETAILED DESCRIPTION

Figure 2:
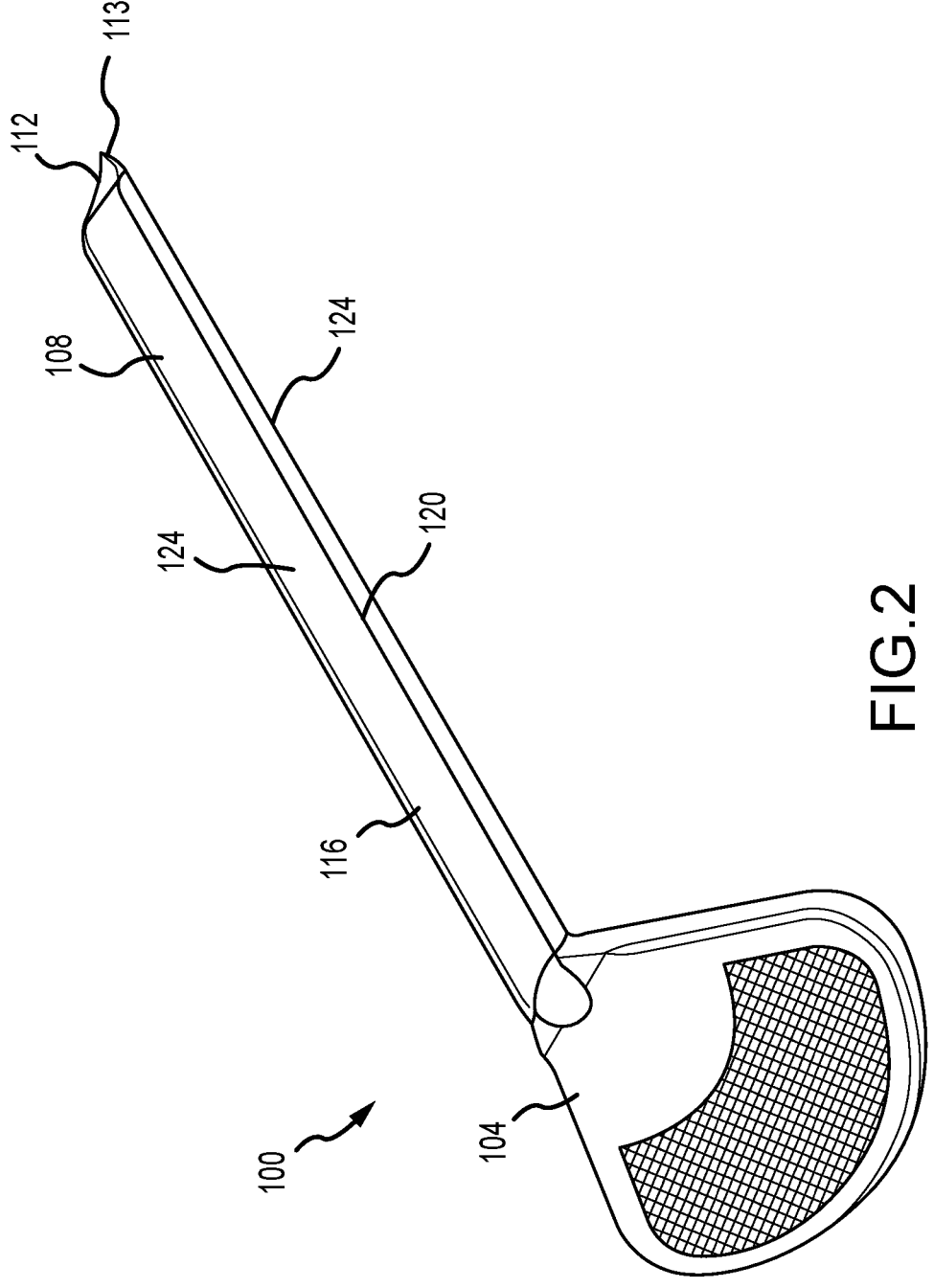
FIG. 2 is an isometric view of the scalpel of FIG. 1A.
Figure 3:
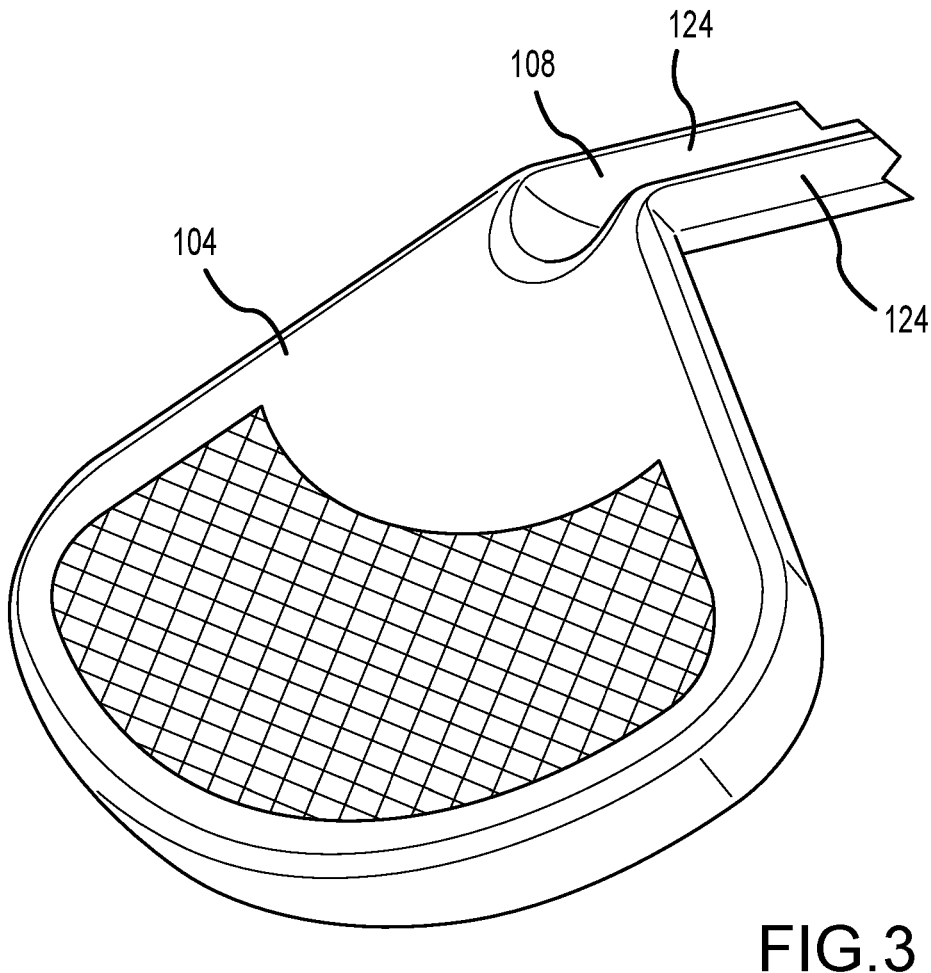
FIG. 3 is an isometric view of the end of the scalpel of FIG. 1A.
Figure 4:
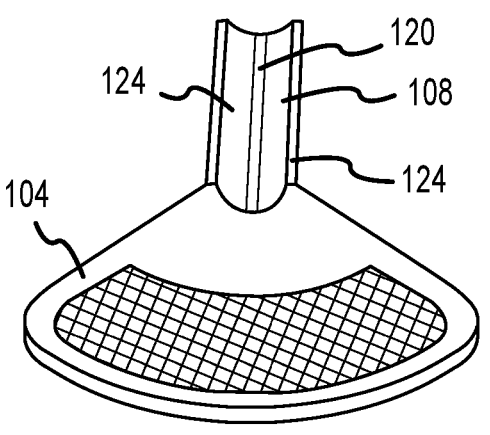
FIG. 4 is another end view of the scalpel of FIG. 1A.

Referring to FIGS. 1A-D and 2-4, a slotted scalpel according to an embodiment of this disclosure is depicted. The slotted scalpel 100 comprises an angled handle 104 that is offset at an angle 122 ranging from about 25 to about 75 degrees from a longitudinal axis 118 of the body 116, a half-pipe longitudinal slot or channel 108 (which can be of varying sizes to accommodate differently sized catheters) extending at least substantially an entire length of the body 116, and tissue cutting metal tip 112 offset at an angle ranging from about 25 to about 75 degrees from the longitudinal axis 118 and having a bevel length ranging from about 2 to about 7 mm that ends in a point 113. The channel 108 surface 128 and opposing lower surface 130 of the slotted scalpel 100 are each arcuate in a cross section view perpendicular to the longitudinal axis 118 to provide reduced cutting resistance relative to body tissue. The angled handle 104 enables the physician to maneuver the body 116 in the abdominal wall to position the tip 112 at the desired location and/or channel 108 in the desired trajectory. The slot or channel 108 receives and guides a catheter into a desired position. Although the slot or channel 108 is depicted as a substantially hemicylindrical or half-pipe configuration, it can have a plurality of other arcuate or curvilinear or angular cross-sectional shapes, such as rectangular, triangular, pentagonal, heptagonal, octagonal, decagonal, trapezoidal, elliptical, oval-like, semicircular, and the like.

To enable CT-scan location of the body 116 of the slotted scalpel 100 when positioned in the patient's body, the body 116 is formed of a composite material comprising a relatively thin central metal portion 120 extending along at least substantially its entire length with the remaining material 124 located on either side of the channel 108 being a polymeric non-resorbable resin, such as a polyacetal, polyethylene, and Teflon, that does not significantly reflect the X-ray spectrum of electromagnetic wave energy resulting in a CT artifact. The relatively thin central metal portion 120 connects to the metal cutting tip 112. As will be appreciated, metal is required by a CT scan for accurate subcutaneous object location but too much metal can cause CT metal artifacts to form, thereby reducing location accuracy.

The radius of the arcuate channel 108 is generally substantially the same as the outer radius of the catheter to be received in the channel 108. Typically, the radius of the arcuate channel 108 ranges from about 75% to about 125% of the outer radius of the catheter.

Figure 5:
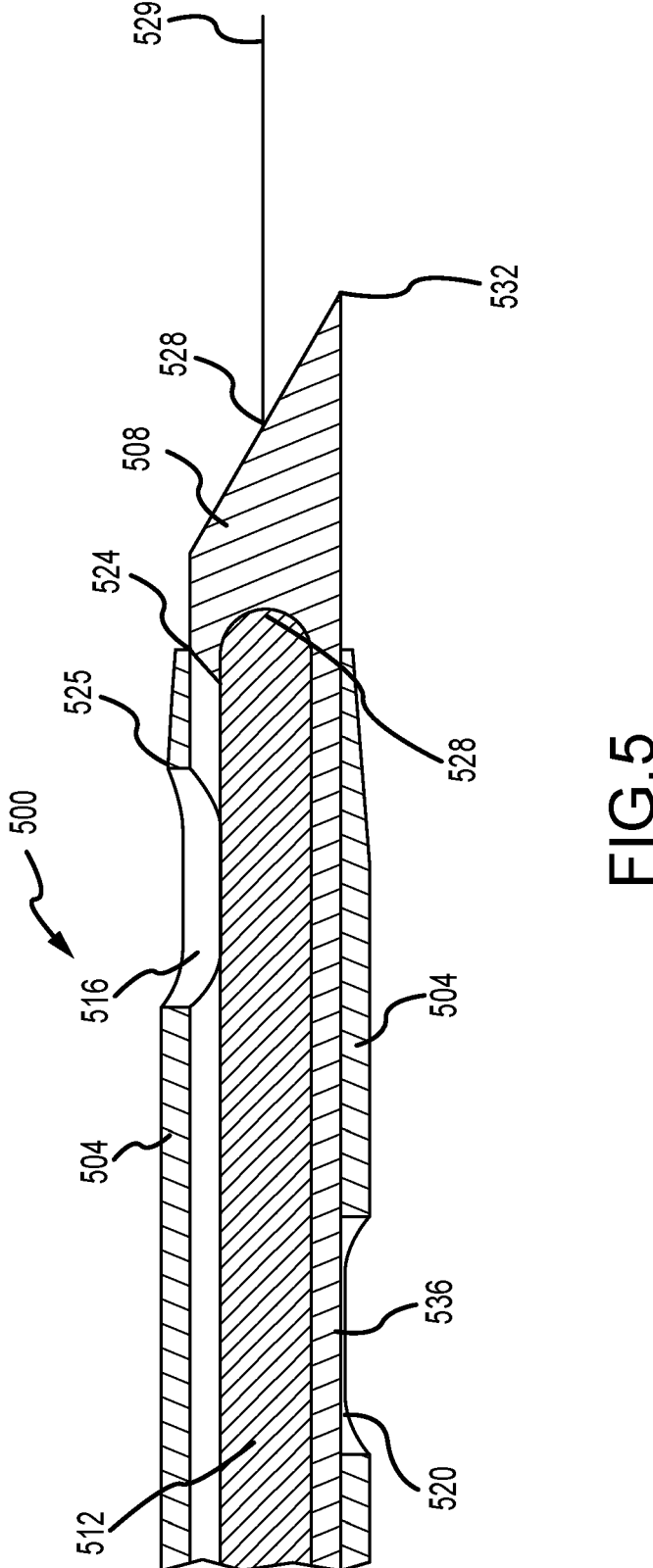
FIG. 5 is a cross-sectional view of a catheter along a longitudinal axis of the catheter according to an embodiment of the present disclosure.
Figure 6:
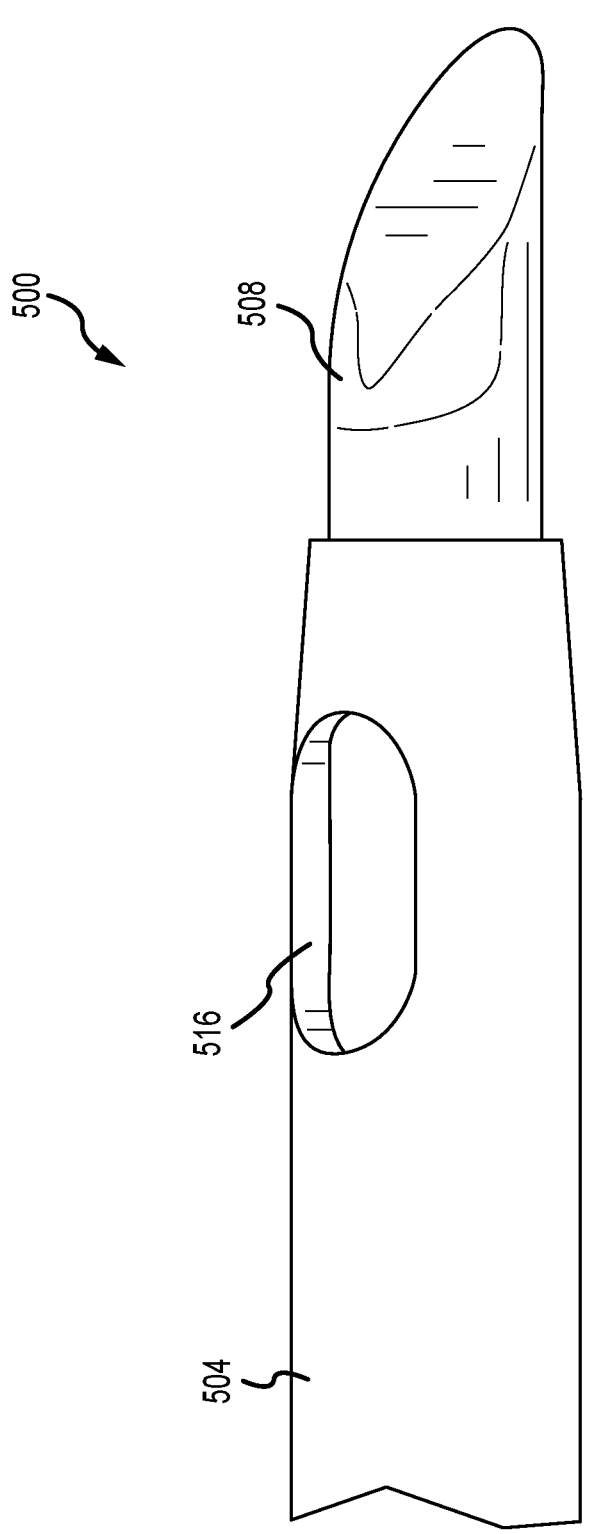
FIG. 6 is an isometric view of a tip of the catheter of FIG. 5.

The flexible catheter assembly 500 will now be described with reference to FIGS. 5-7. The catheter assembly 500 comprises a tubular catheter body 504, an outer stylet 508, and inner stylet 512. Although the catheter assembly 500 is depicted as substantially cylindrical, it can have a plurality of other arcuate or curvilinear cross-sectional shapes, such as elliptical, oval-like, semicircular, and the like.

The catheter body 504 comprises an aspiration port 516 and plural drainage ports 520 positioned along a length of the catheter body 504. The aspiration port 516 and drainage ports 520 are on opposing sides of the catheter body 504. While the aspiration port 516 and plurality of drainage ports 520 are shown as being substantially the same orifice sizes, it is to be appreciated that the ports can be of different sizes depending on the application.

The inner stylet 512 is substantially solid and moves, independently of the catheter body 504 and outer stylet 508, laterally back and forth along a longitudinal axis of the catheter body 504 to open or close the aspiration port 516. The inner stylet 512 is normally in the forward position shown in FIG. 5 during insertion of the catheter assembly 500 along the channel 108 into the body of the patient to maintain the aspiration port 516 closed. When the catheter is in or near the abscess, the inner stylet 512 is removed, by rearward displacement, from the catheter body 504 (as shown in FIG. 6) to open the aspiration port and provide a first catheter lumen. The open aspiration port 516 and first lumen provide a fluid flow path enabling the operator to confirm by observed abscess fluid (e.g., pus) drainage along the path of flow that the catheter body 504 is positioned a selected depth in the abscess. The distance of a forward edge 525 of the aspiration port from a free end 524 of the catheter assembly can be selected to confirm that the catheter assembly is a safely selected distance within the abscess. In typical applications, the distance between the forward edge 525 and the free or distal end 524 ranges from about 0.5 to about 2.5 cm and more typically from about 0.5 to about 2 cm.

The outer stylet 508 is in a half-pipe configuration and is configured to receive and enable lateral movement of the inner stylet 512 back and forth along the first lumen of the catheter body 504 and comprises a solid core beveled tissue cutting tip 528 having a point 532. When the outer stylet is in the extended position shown in FIG. 5, the drainage ports are closed to fluid drainage by the body 536 of the outer stylet 508. When the catheter assembly 500 is positioned in the abscess, the outer stylet is removed by lateral rearward displacement from the catheter body 504 to form a second lumen, thereby opening the drainage ports to abscess fluid drainage along the second lumen. The second lumen comprises both the first lumen (or volume formerly occupied by the inner stylet 512) and the volume formerly occupied by the outer stylet 508. The bevel length of the beveled tip 528 and downward angle from a catheter assembly longitudinal axis 529 is typically substantially the same as that of the slotted scalpel 100.

Because the inner and outer stylets 512 and 508 are independently moveable from each other and the catheter body within the catheter body, the inner stylet 512 can be removed to open the aspiration port 516 and form the first lumen while leaving the outer stylet 508 in position to close the drainage ports 520. This configuration of the catheter assembly 500 is shown in FIG. 6.

The spatial poisoning of the drainage ports 516 and 520 can vary depending on the application. In typical applications, the distance between opposing edges of the drainage ports ranges from about 0.5 to about 2.5 cm.

Figure 7:
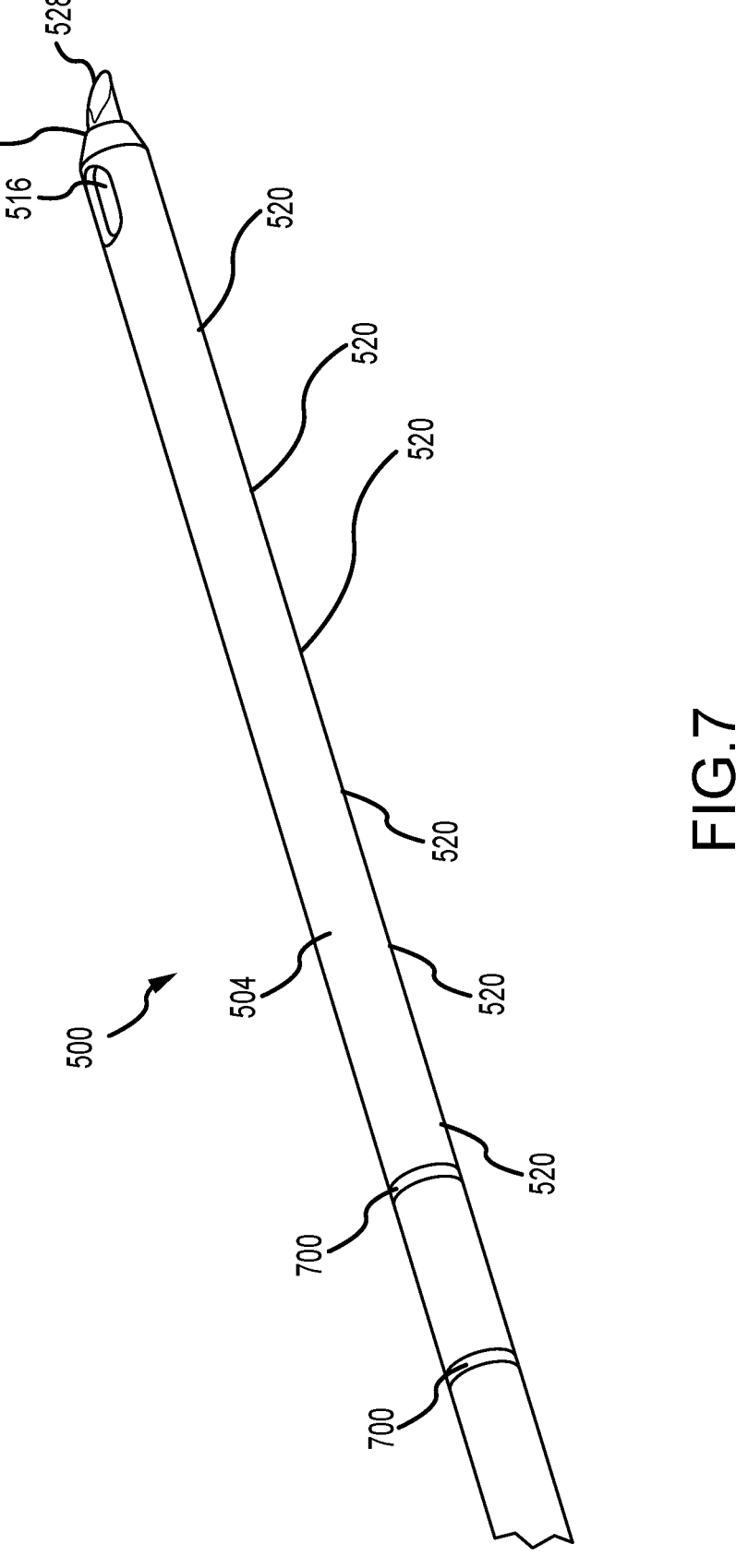
FIG. 7 is an isometric view of the top of the catheter of FIG. 5.

With reference to FIG. 7, the catheter assembly 500 can include distance markers 700 to enable a physician to gauge an approximate position of the catheter tip 528 in the patient's body relative to a selected reference point, such as the location of the incision in the patient's skin. The distance markers 700 are typically indexed relative to a free end of the catheter body 524 or the beveled point 528. In one configuration, a distance of a first distance marker 700 on the catheter relative to the catheter tip 528 equals a length of the channel 108 to enable a physician to align or collocate or stack the catheter tip 528 with the metal cutting tip 112.

A method of using the slotted scalpel 100 and catheter assembly 500 will now be described with reference to FIGS. 8A-B and 9-21. By way of background, FIG. 9 depicts a typical condition to be treated. An abscess 900 has formed in the patient's intraperitoneal fat 904 located beneath the patient's skin 908, subcutaneous fat 912, and muscle 916.

Figure 8A:
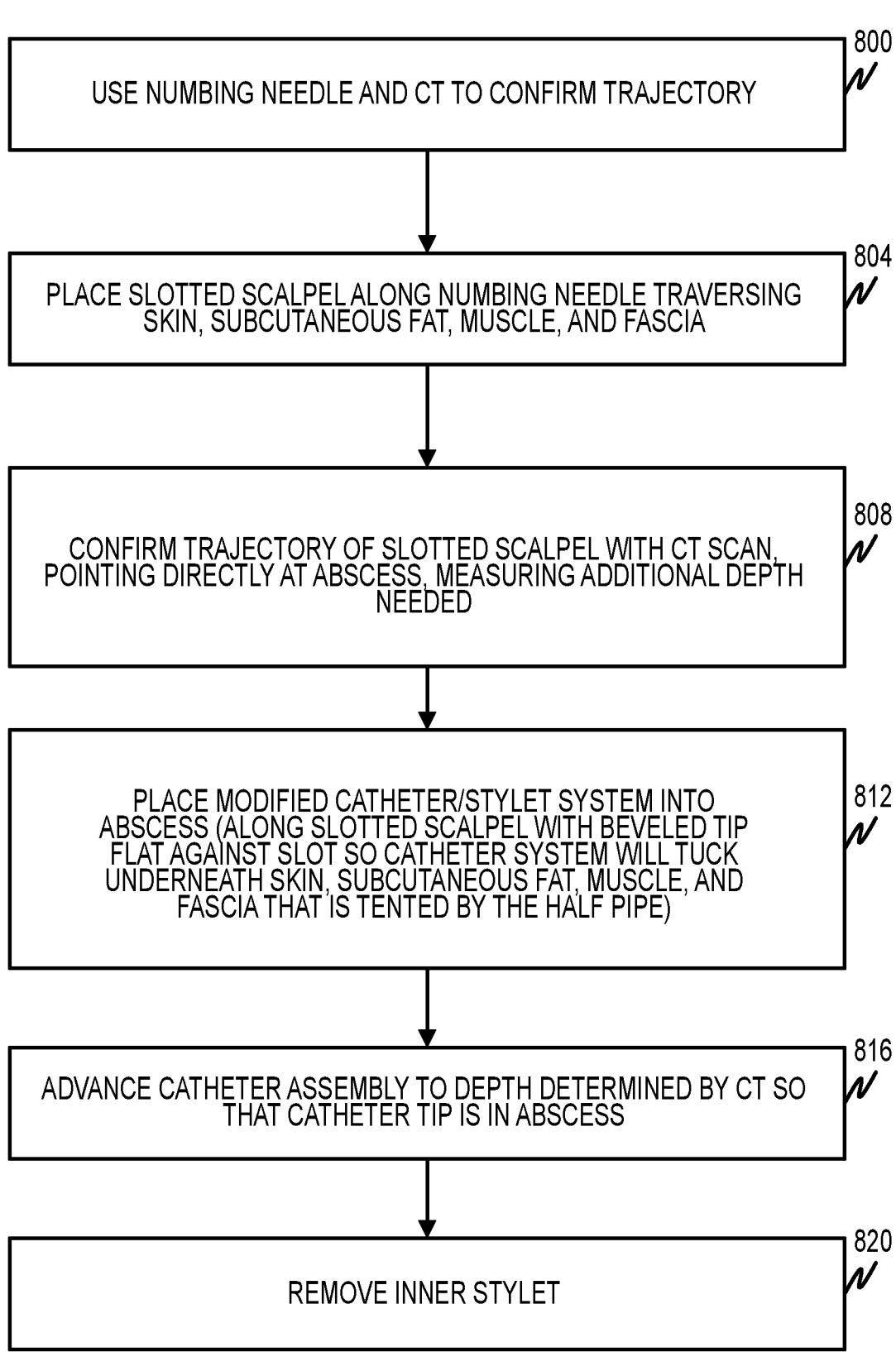
FIG. 8A is a surgical method according to an embodiment of the present disclosure.
Figure 8B:
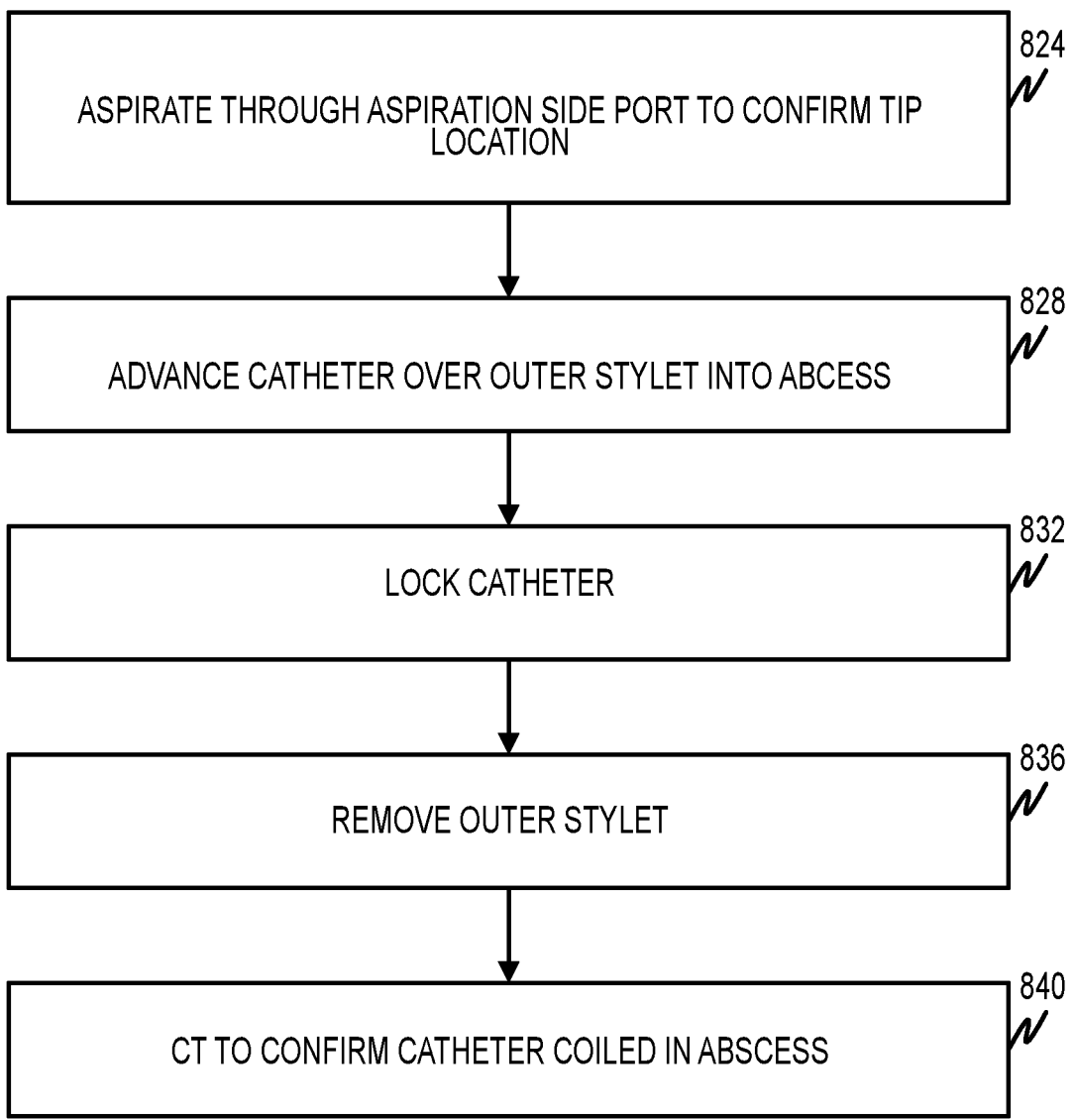
FIG. 8B is a surgical method according to an embodiment of the present disclosure.
Figure 9:
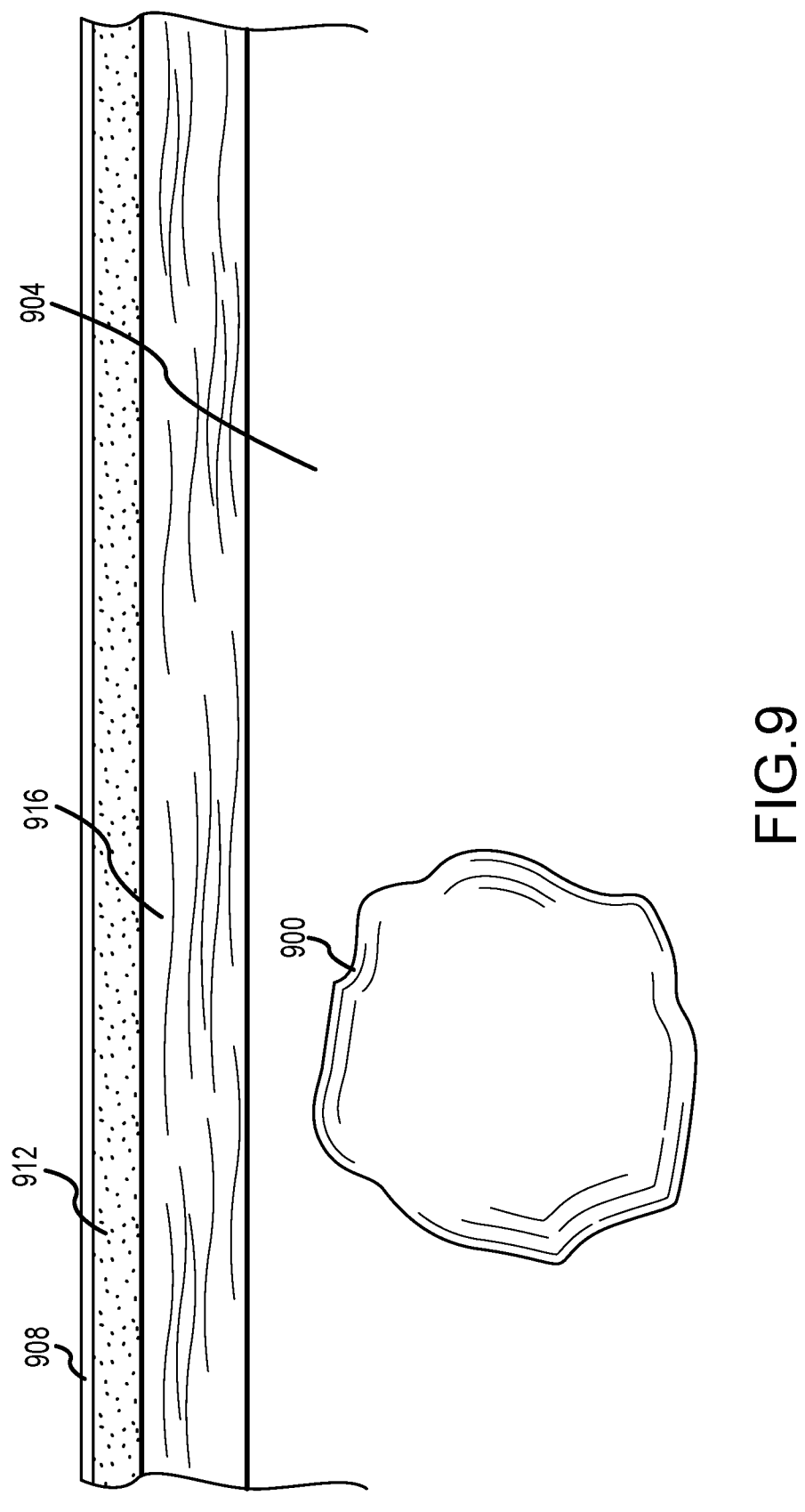
FIG. 9 shows a subcutaneous abscess according to an embodiment of the present disclosure.
Figure 10:
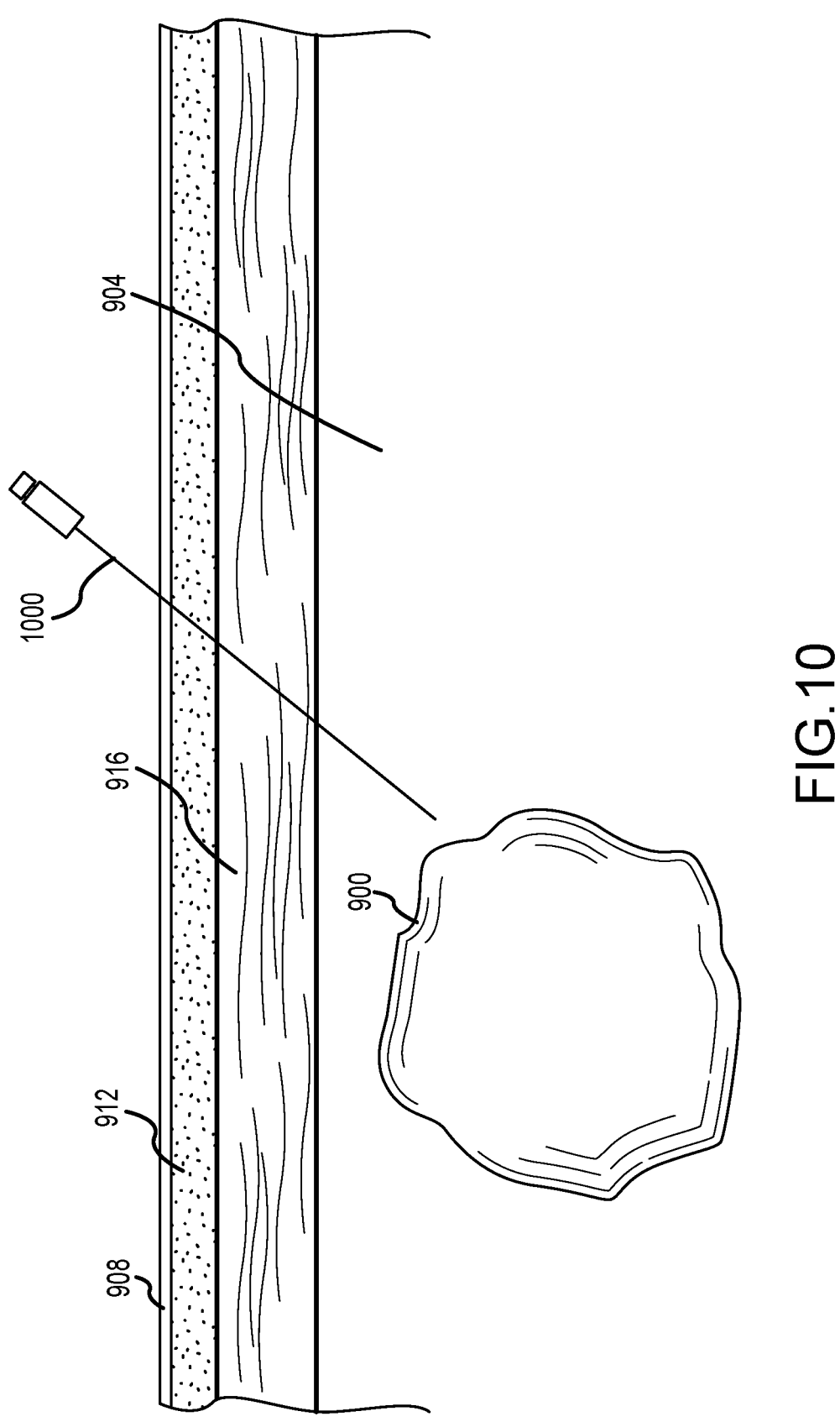
FIG. 10 shows a hypodermic needle being inserted into the abscess according to an embodiment of the present disclosure.

With step 800 of reference to FIG. 8A, to drain the abscess 900 the physician in step 800 uses a numbing needle and a CT scanner to confirm a needle trajectory in the patient, and the patient is thereafter removed from the CT gantry. With reference to FIG. 10, the numbing needle 1000 is injected through the skin 908, subcutaneous fat 912, muscle 916, and fascia intraperitoneal fat 904 to a location near the abscess 900. The CT scan enables the physician to locate the trajectory and position of the needle point relative to the abscess 900. The physician then numbs the needle tract profusely.

In step 804, the physician makes a superficial incision with the slotted scalpel 100 and places the slotted scalpel 100 along the numbing needle and traverses the through the skin 908, subcutaneous fat 912, muscle 916, and fascia intraperitoneal fat 904 to a location near the abscess 900

Figure 11:
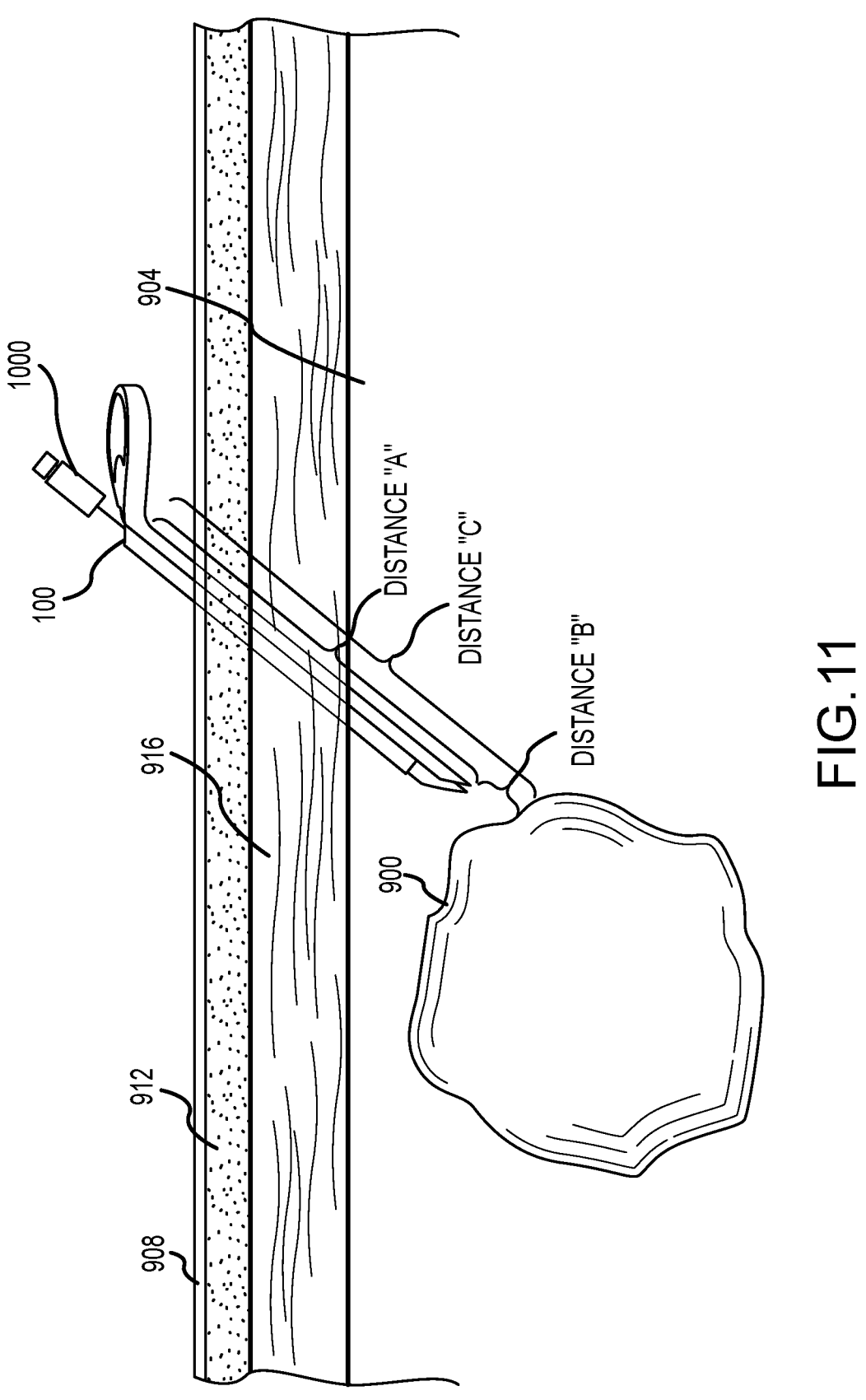
FIG. 11 shows a channel of a scalpel being inserted along a length of the hypodermic needle according to an embodiment of the present disclosure.
Figure 21:
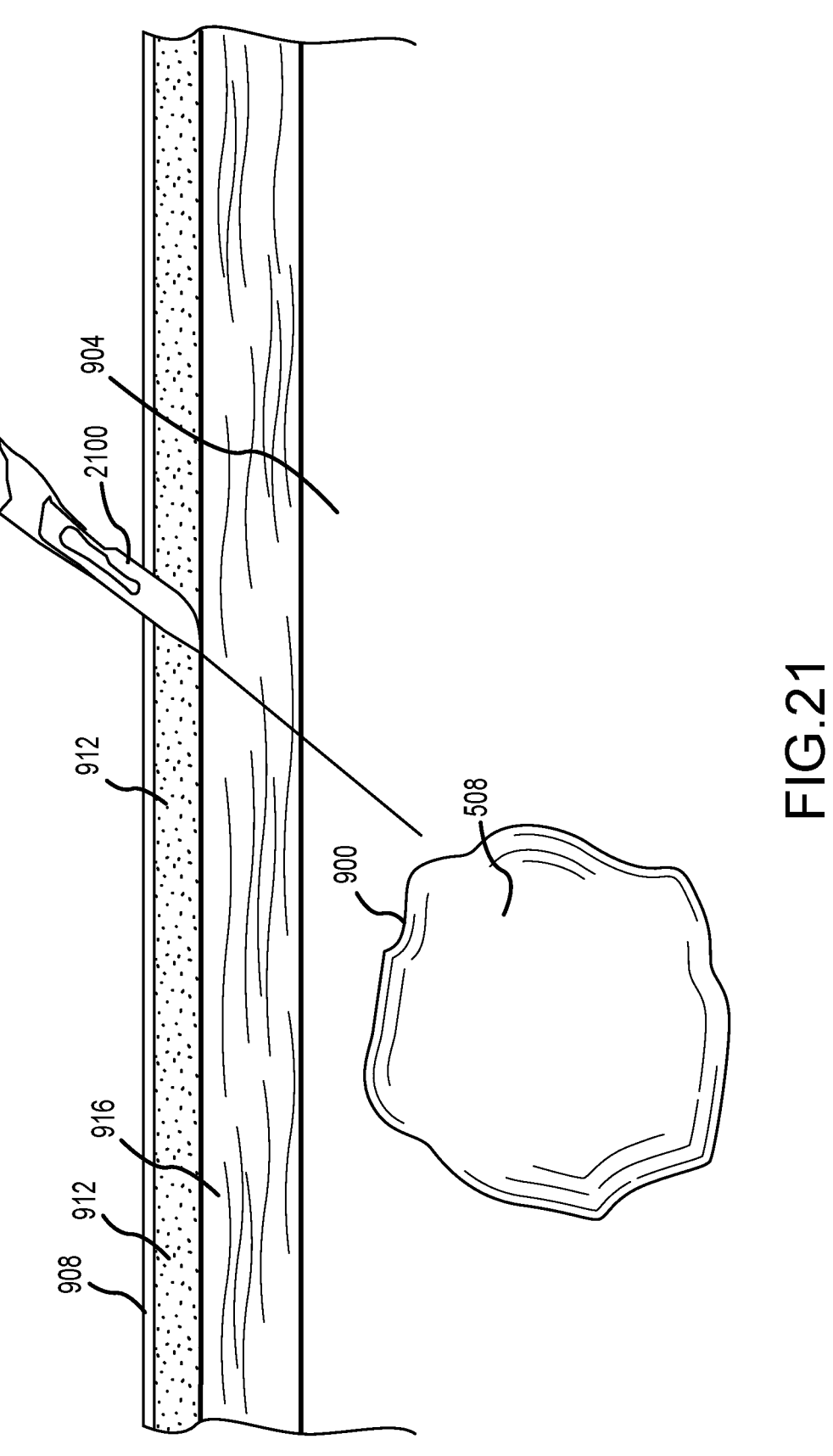
FIG. 21 shows a further scalpel being used to cut a path through the patient's skin according to an embodiment of the present disclosure.

(FIG. 11). The cannula of the needle is received in the channel 108 and guides the cutting metal tip 112 of the slotted scalpel into position near the abscess. Prior to placement of the slotted scalpel 100, the physician can use the numbing needle as a guide to create an incision through the skin 908 and subcutaneous fat 912 to accommodate the cutting metal tip 112 of the slotted scalpel (FIG. 21).

In step 808, the physician confirms the trajectory and position of the slotted scalpel 100 with a CT scanner to confirm that the scalpel 100 is pointing directory at the abscess as shown in FIG. 11, measuring additional depth as needed. In one implementation, the physician measures the distances "A", "B", and "C" in FIG. 11, where distance "A"+distance "B"=total distance "C" from the base of the angled handle or end of the channel to the abscess with the distance measured along a trajectory of the channel. When the slotted scalpel 100 is properly positioned, the physician removes the patient from the CT gantry and removes the numbing needle 1000 from the patient's body.

In step 812, the physician positions the catheter assembly 500 into the channel 108 (which is configured to receive both the numbing needle 1000 and the catheter assembly 500) and, with the beveled tip flat against the slot, advances the tip of the catheter assembly along the channel 108. The beveled tip forces the catheter assembly to hug the deepest portion of the channel 108. This catheter assembly position relative to the channel 108, ensures that the catheter assembly 500 will tuck underneath the skin, subcutaneous fat, muscle, and fascia that is tented by the half-pipe shape of the body 116 of the slotted scalpel 100.

Figure 12:
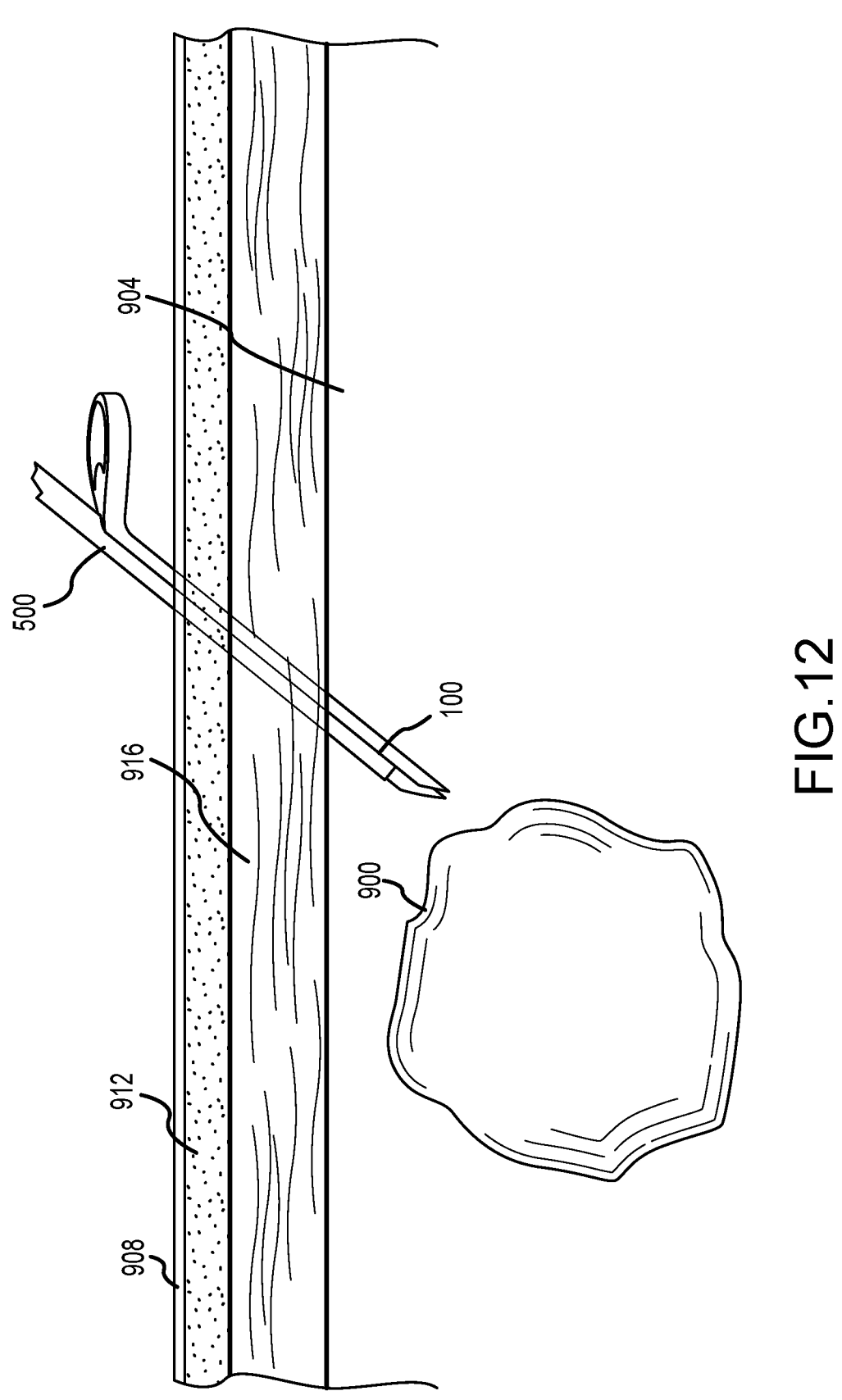
FIG. 12 shows, after needle removal, a catheter being inserted into the channel of the scalpel according to an embodiment of the present disclosure.
Figure 13:
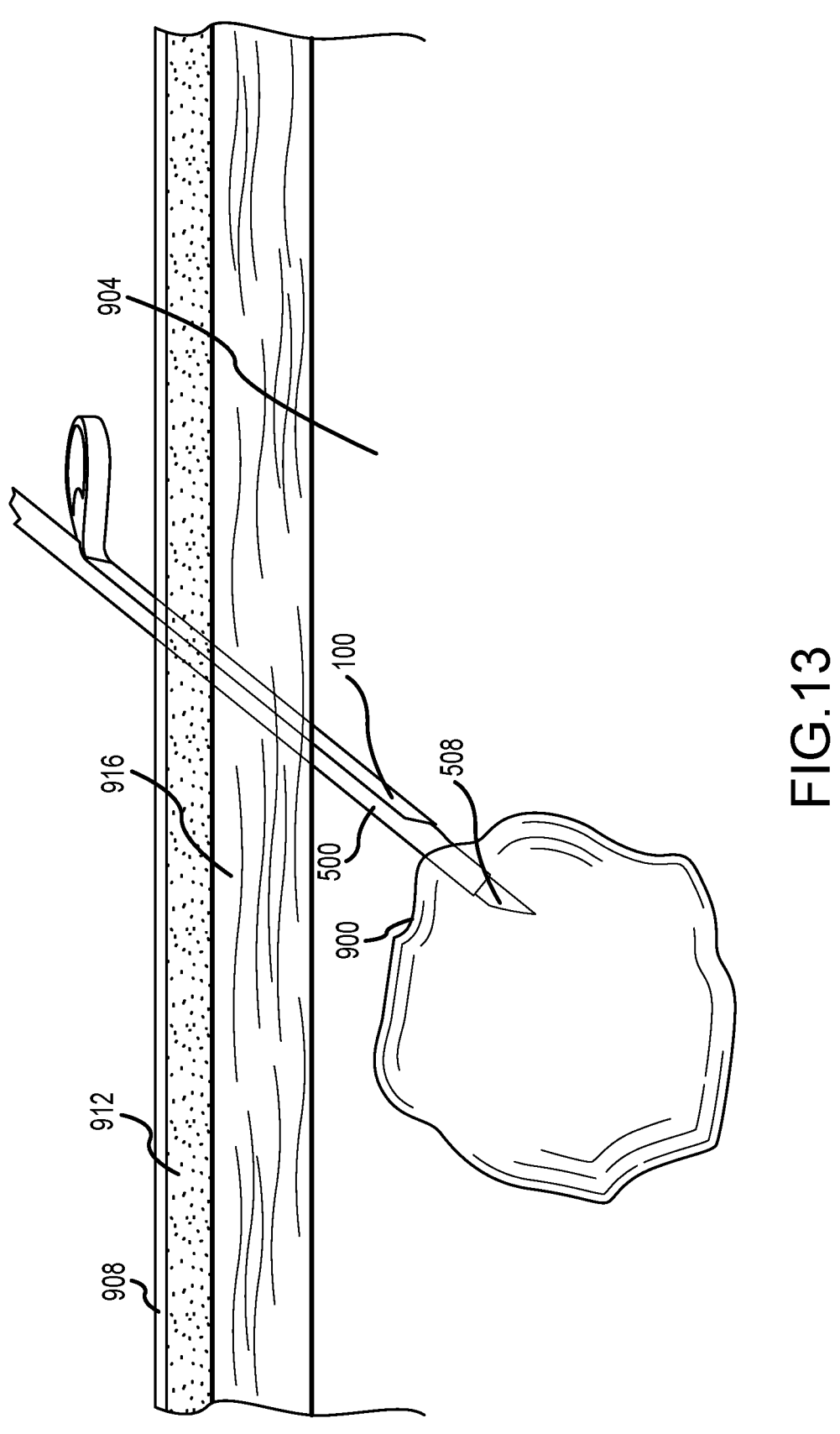
FIG. 13 shows the catheter being guided along the scalpel channel into the abscess according to an embodiment of the present disclosure.
Figure 14A:
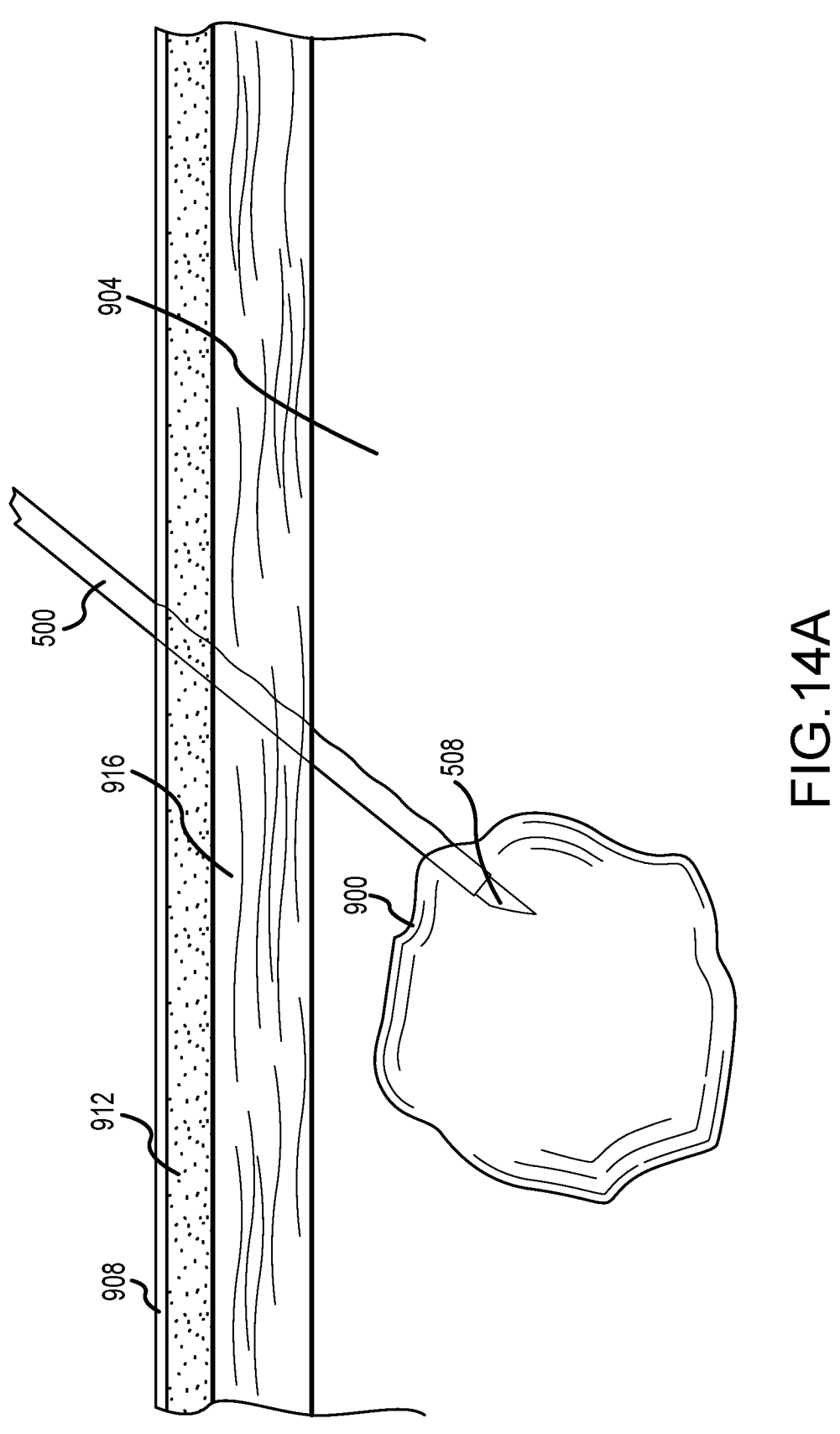
FIG. 14A shows, after scalpel removal, the catheter inserted into the abscess according to an embodiment of the present disclosure.
Figure 14B:
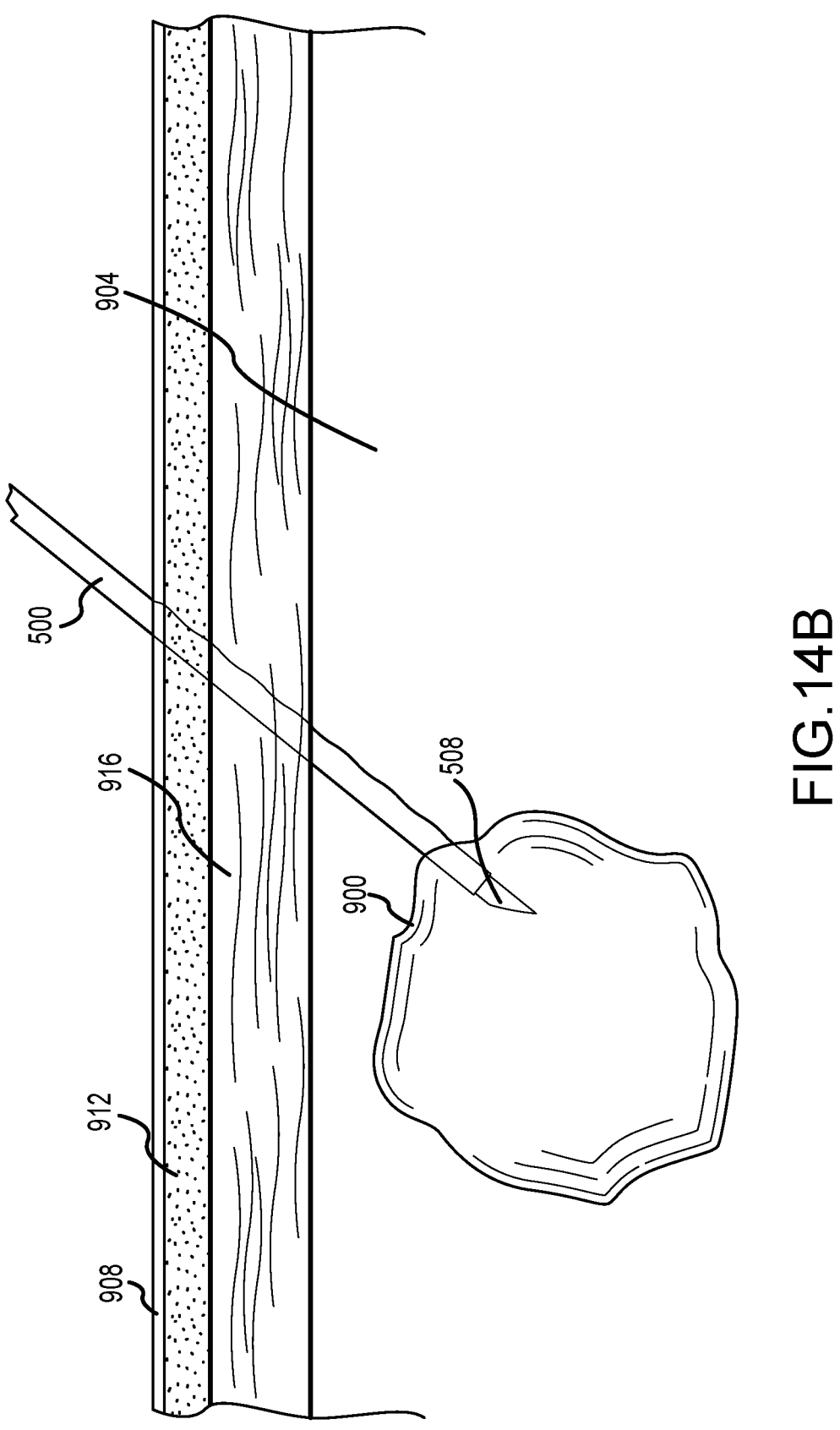
FIG. 14B shows, after scalpel removal, the catheter inserted into the abscess according to an embodiment of the present disclosure.
Figure 22:
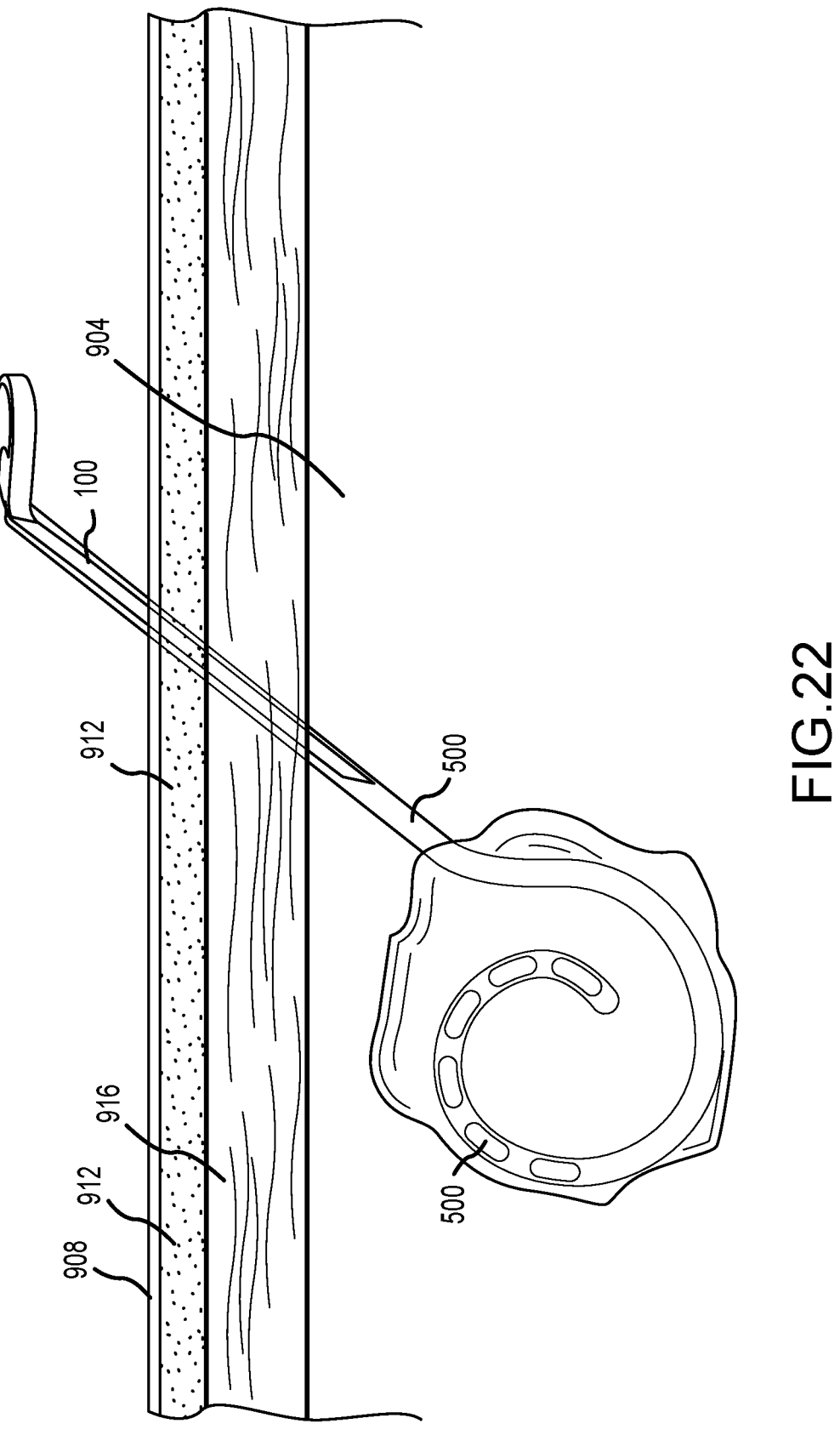
FIG. 22 shows the catheter being inserted further into the abscess using the scalpel channel according to an embodiment of the present disclosure.
Figure 24:
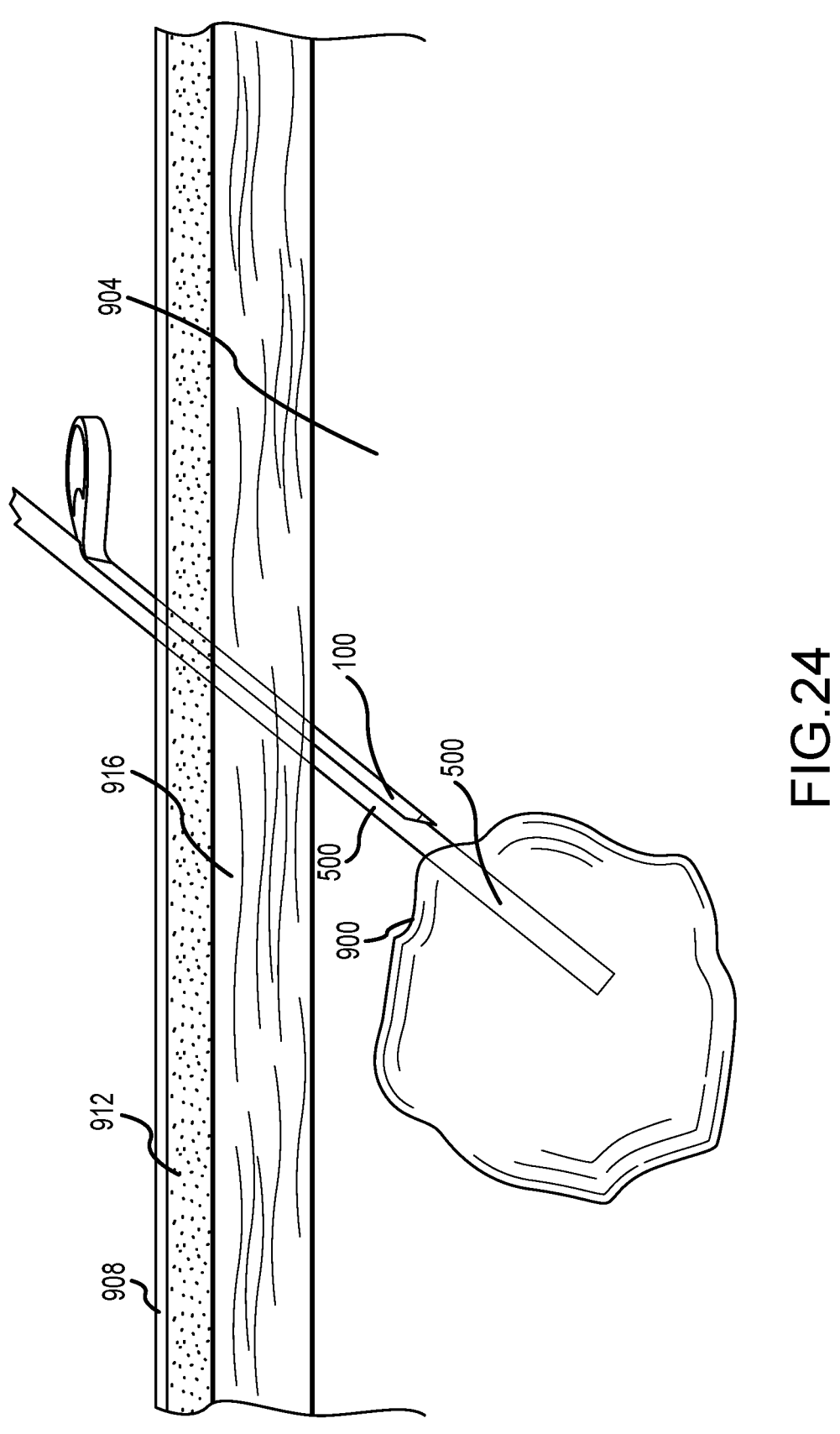
FIG. 24 shows the catheter being inserted further into the abscess using the scalpel channel according to an embodiment of the present disclosure.

In step 816, the physician advances the catheter assembly 500 to a depth determined by the CT scans of step 808 so that the catheter tip is in the abscess 900. This placement is depicted in FIGS. 12-13. When the catheter assembly 500 is positioned properly, the scalpel 100 can be then removed along the body 524 of the catheter assembly 500 as shown in FIGS. 14A-B. In other process embodiments shown in FIGS. 22 and 24, the scalpel 100 is removed only after steps 820 and 824, or after abscess fluid drainage through the aspiration port confirms that the catheter is correctly positioned in the abscess 900. Stated differently, FIGS. 22 and 24 show that the slot of the scalpel is used to guide the catheter assembly 500 deeper into the abscess 500 prior to slotted scalpel removal. In other embodiments, the scalpel 100 is removed after step 828, 832, and/or 836.

Figure 15:
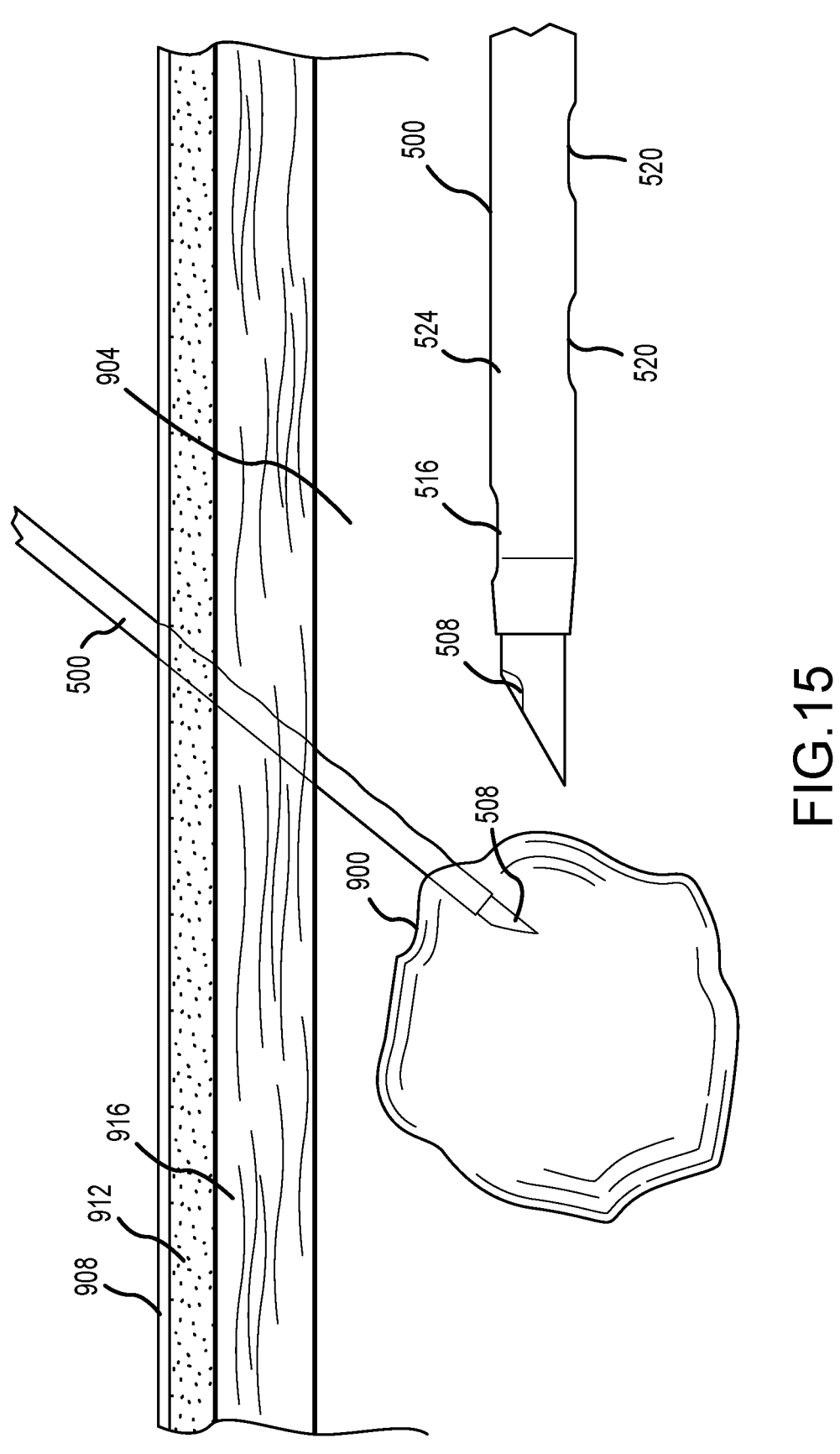
FIG. 15 shows additional detail of the catheter that is inserted into the abscess according to an embodiment of the present disclosure.
Figure 16:
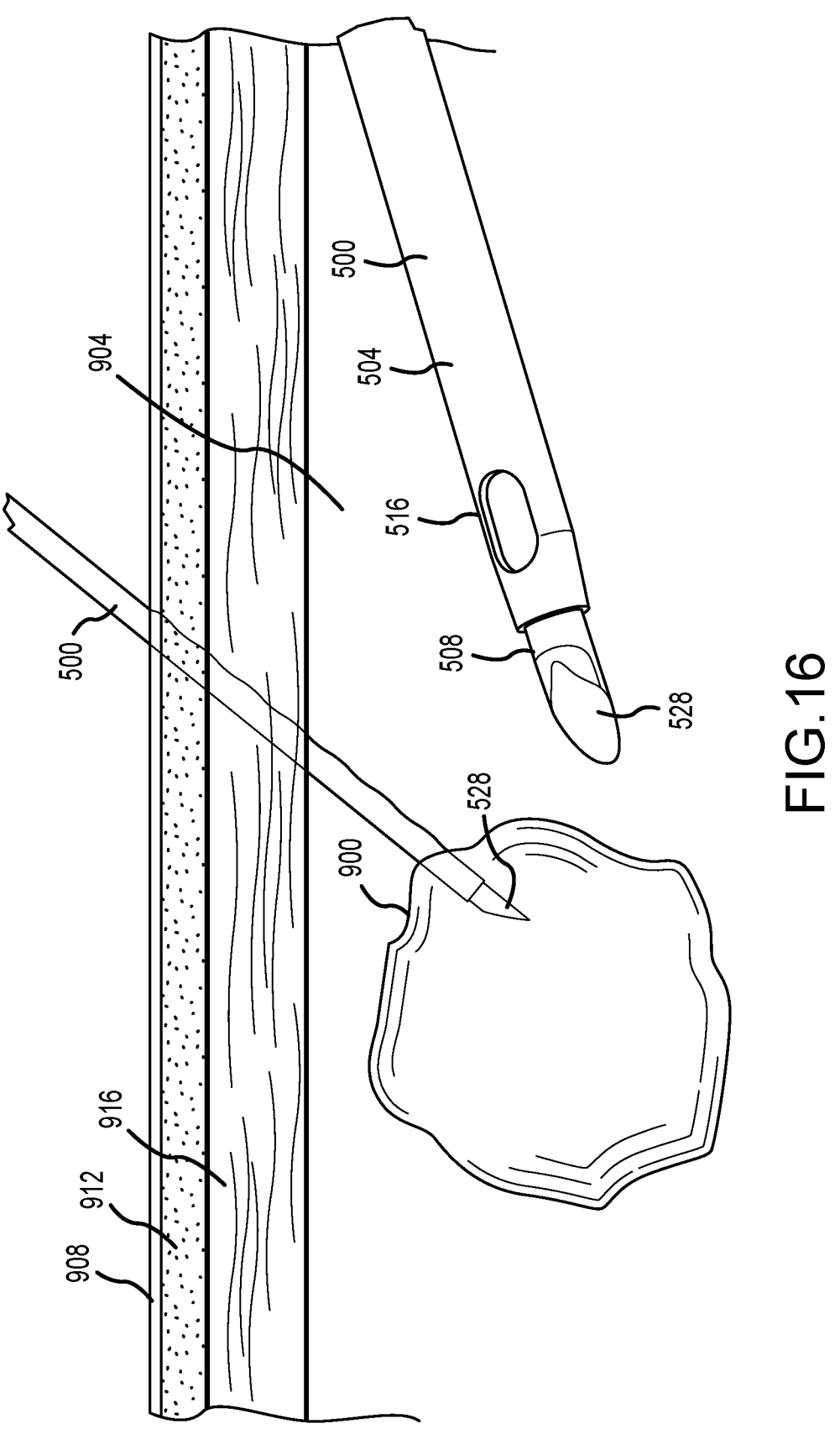
FIG. 16 shows additional detail of the catheter that is inserted into the abscess according to an embodiment of the present disclosure.
Figure 17:
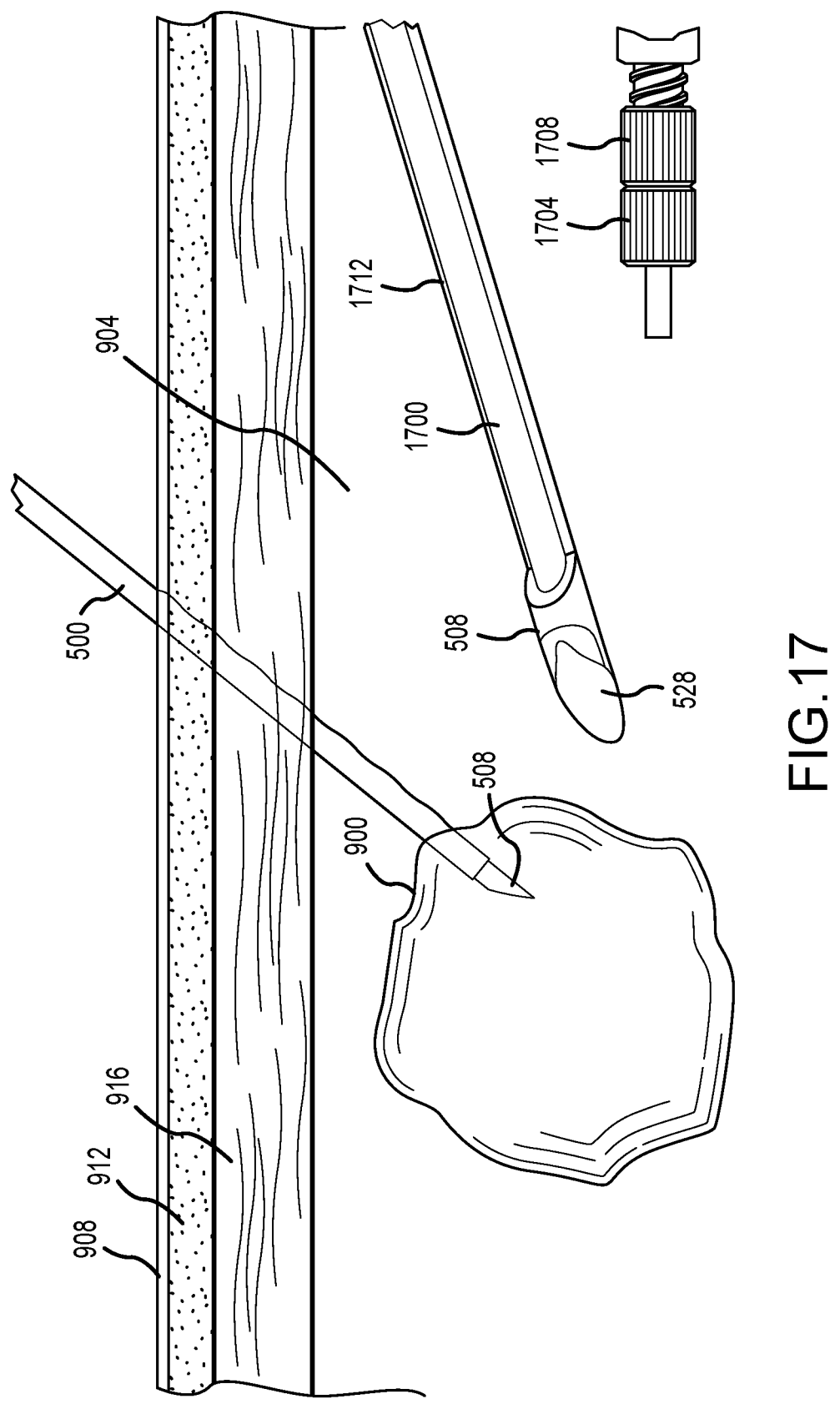
FIG. 17 shows additional detail of the catheter that is inserted into the abscess according to an embodiment of the present disclosure.
Figure 18:
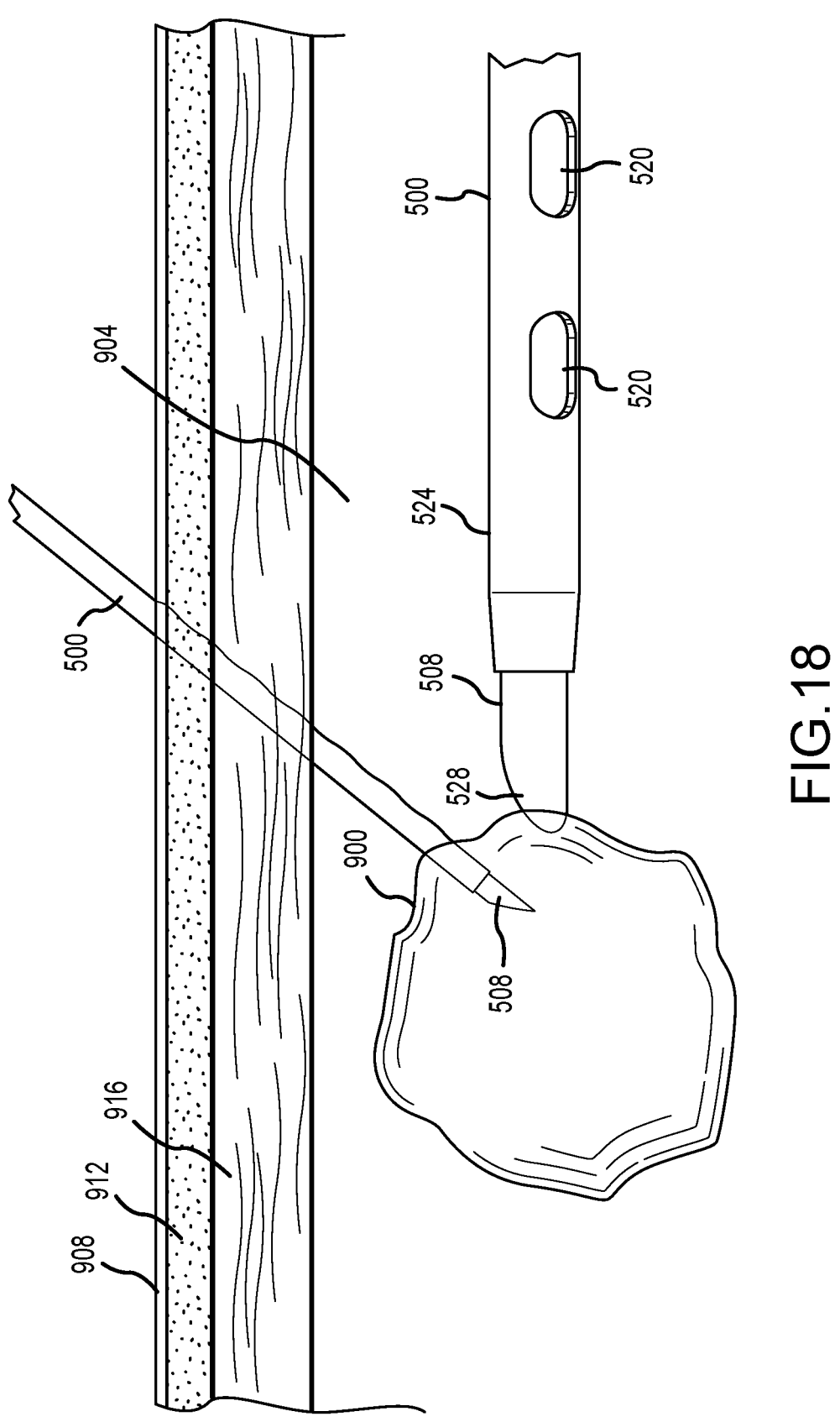
FIG. 18 shows additional detail of the catheter that is inserted into the abscess according to an embodiment of the present disclosure.
Figure 23:
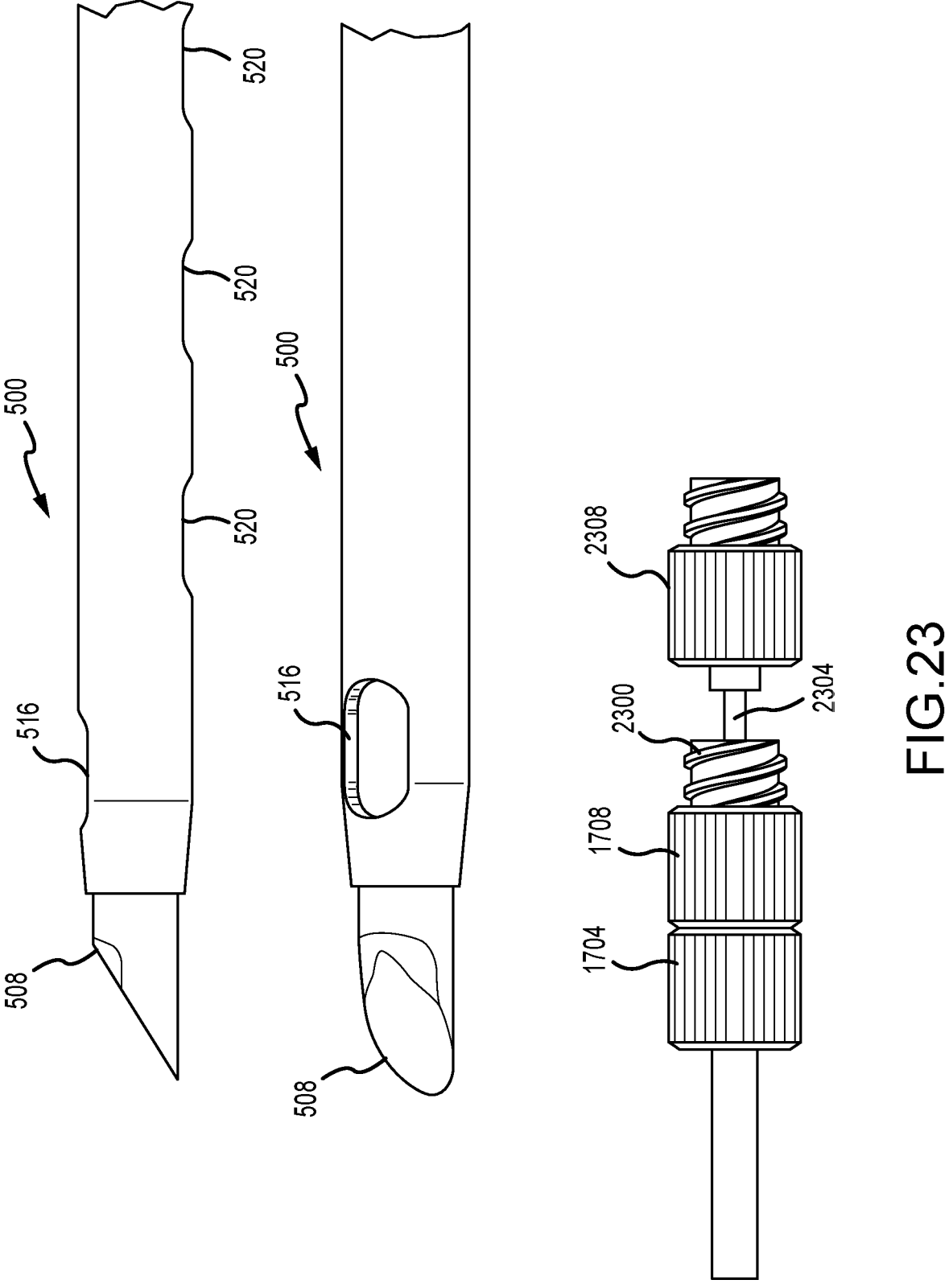
FIG. 23 shows a catheter configuration according to an embodiment of the present disclosure.

In step 820, the physician removes the inner stylet 524 from the catheter body 504 to open the first lumen along the length of the catheter assembly 500 while leaving the outer stylet 508 in a forward position. This catheter configuration is shown in FIGS. 15-16 and 18. FIG. 17 shows additional detail on the outer stylet 508. The tip 528 is solid, fills the open distal end of the body 500, and forms a seal with the interior surface of the distal opening that is substantially impervious to fluid flow. The body 1700 of the outer stylet 508, like the slotted scalpel 100, includes a half-pipe longitudinal slot or channel 1712 to channel abscess fluid flow along the catheter body 524. FIG. 17 further shows the outer stylet 508 in position after removal of the inner stylet 512. FIG. 17 specifically shows the half-pipe drainage channel design of the inner surface of the outer stylet and the opposing upper and lower arcuate surfaces of the outer stylet in a cross-sectional view perpendicular to a longitudinal axis of the catheter assembly. Rotatable interlocking user manipulators 1704 and 1708 enable inner and outer stylet interlocking and removal. As shown in FIG. 23, the inner stylet 512 is removed by unscrewing an inner stylet threaded interlocking user manipulator 2308 (which is connected to the inner stylet by elongated member 2304) from an outer stylet threaded interlocking user manipulator 1708 (by unscrewing the manipulator 2308 from the threaded portion 2300 of the manipulator 1708), which is, in turn, threadedly connected to a threaded interlocking user manipulator 1704 of the catheter assembly 500. The interlocking manipulators can act as a locking mechanism to maintain the inner and outer stylets in a desired relative position during insertion.

Figure 25:
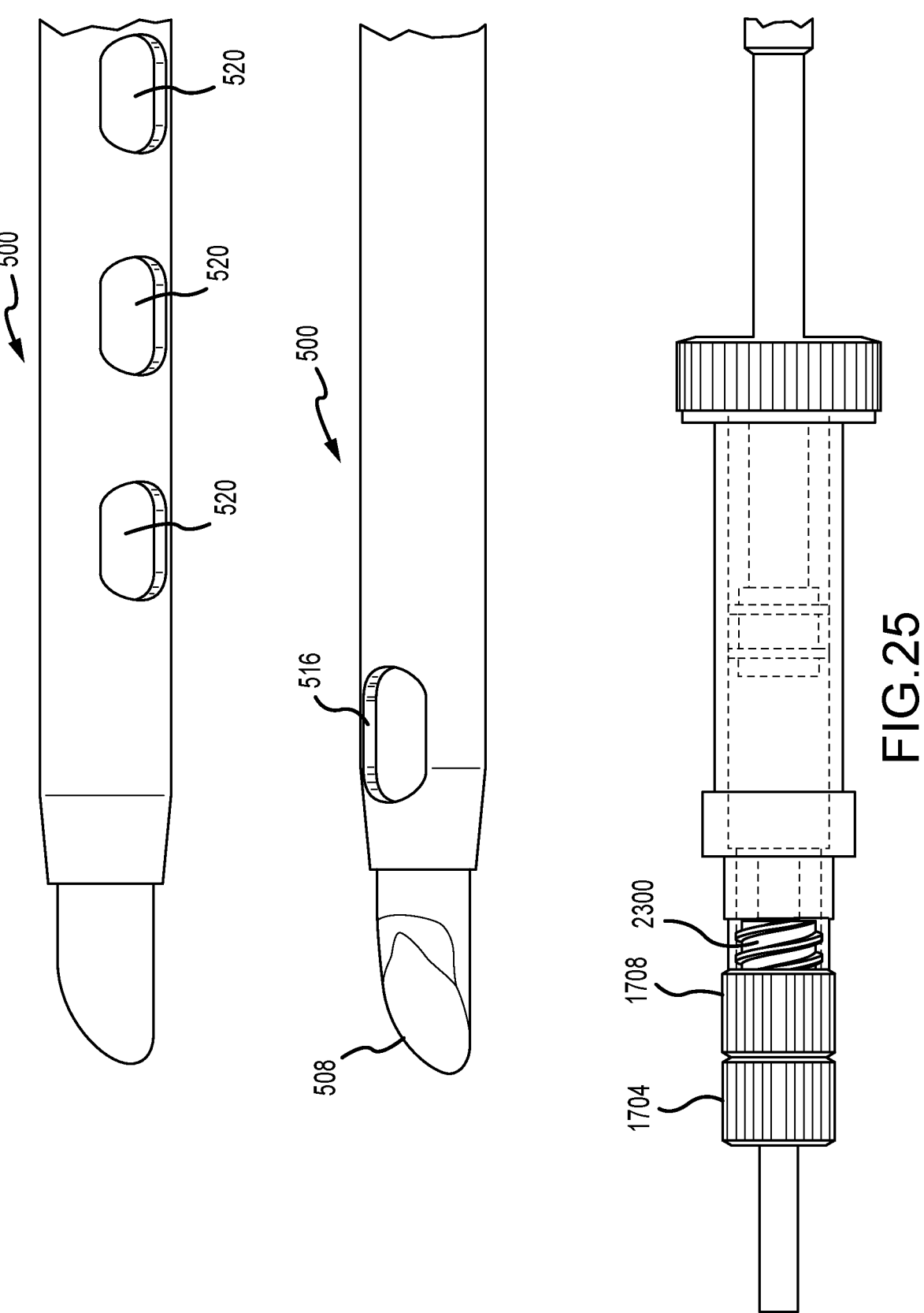
FIG. 25 shows a catheter configuration according to an embodiment of the present disclosure.
Figure 26:
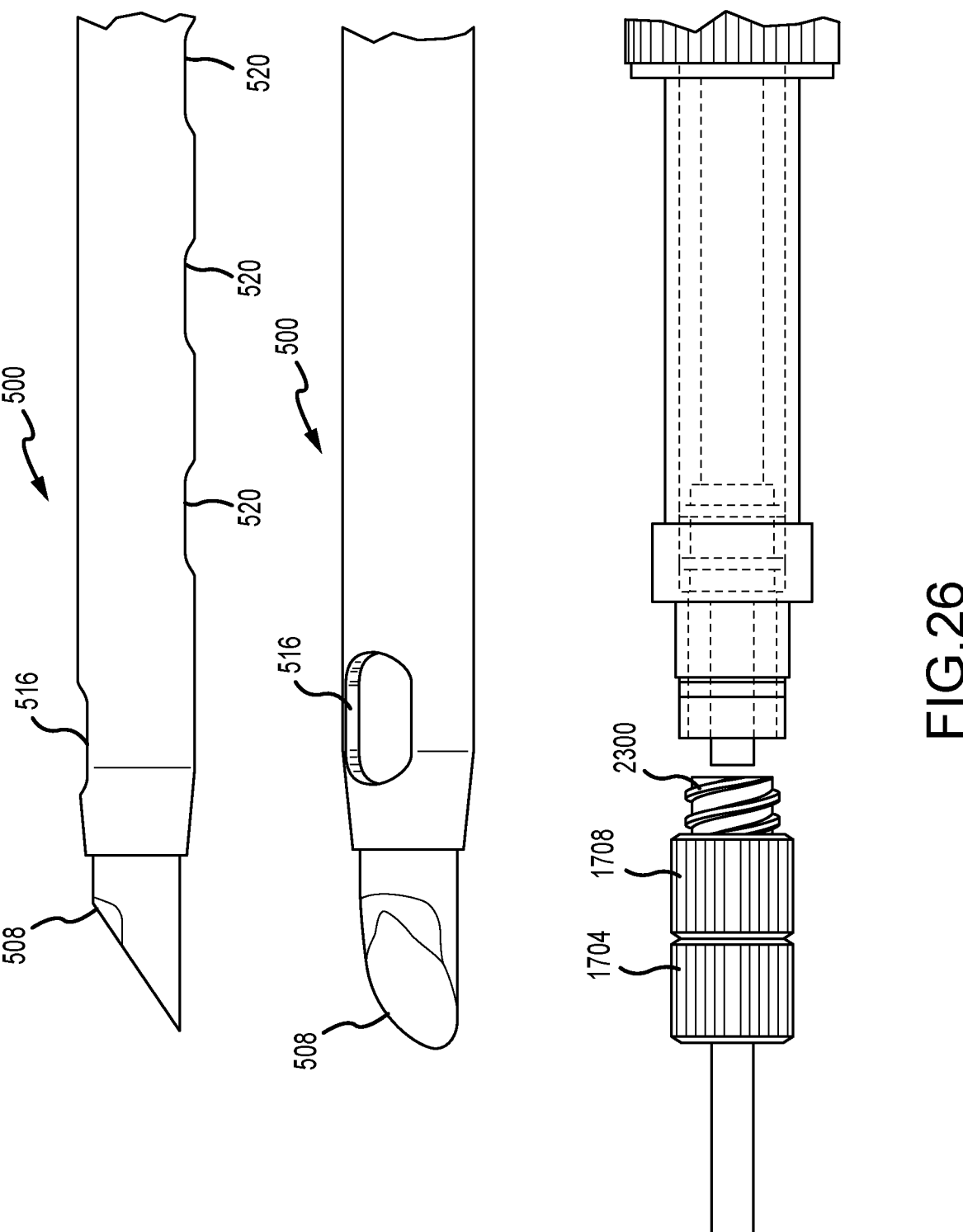
FIG. 26 shows a catheter configuration according to an embodiment of the present disclosure.

In step 824, the abscess fluid aspirates through the aspiration port and through the first lumen and thereby confirms to the physician that the tip 528 location. When necessary, a suction source, such as the plunger and seal and barrel of a syringe, to draw abscess fluid along the first lumen for such confirmation. This configuration is shown in FIGS. 25 and 26 in which a plunger 2500 and seal 2504 and barrel 2508 of a syringe 2512 are threadedly connected to the outer stylet threaded interlocking user manipulator 1708 via the threaded portion 2300 (while the drainage ports remain blocked and closed by the outer stylet body) and the plunger and seal drawn back to create a suction in the barrel for the abscess fluid.

In step 828, the physician advances the catheter body 504 along the outer stylet, while holding the outer stylet 508 in a substantially stationary position, into the abscess so that the second lumen opens to enable abscess fluid drainage through not only the aspiration port 516 but also the drainage ports 520 into the second lumen resulting from outer stylet removal.

Figure 20:
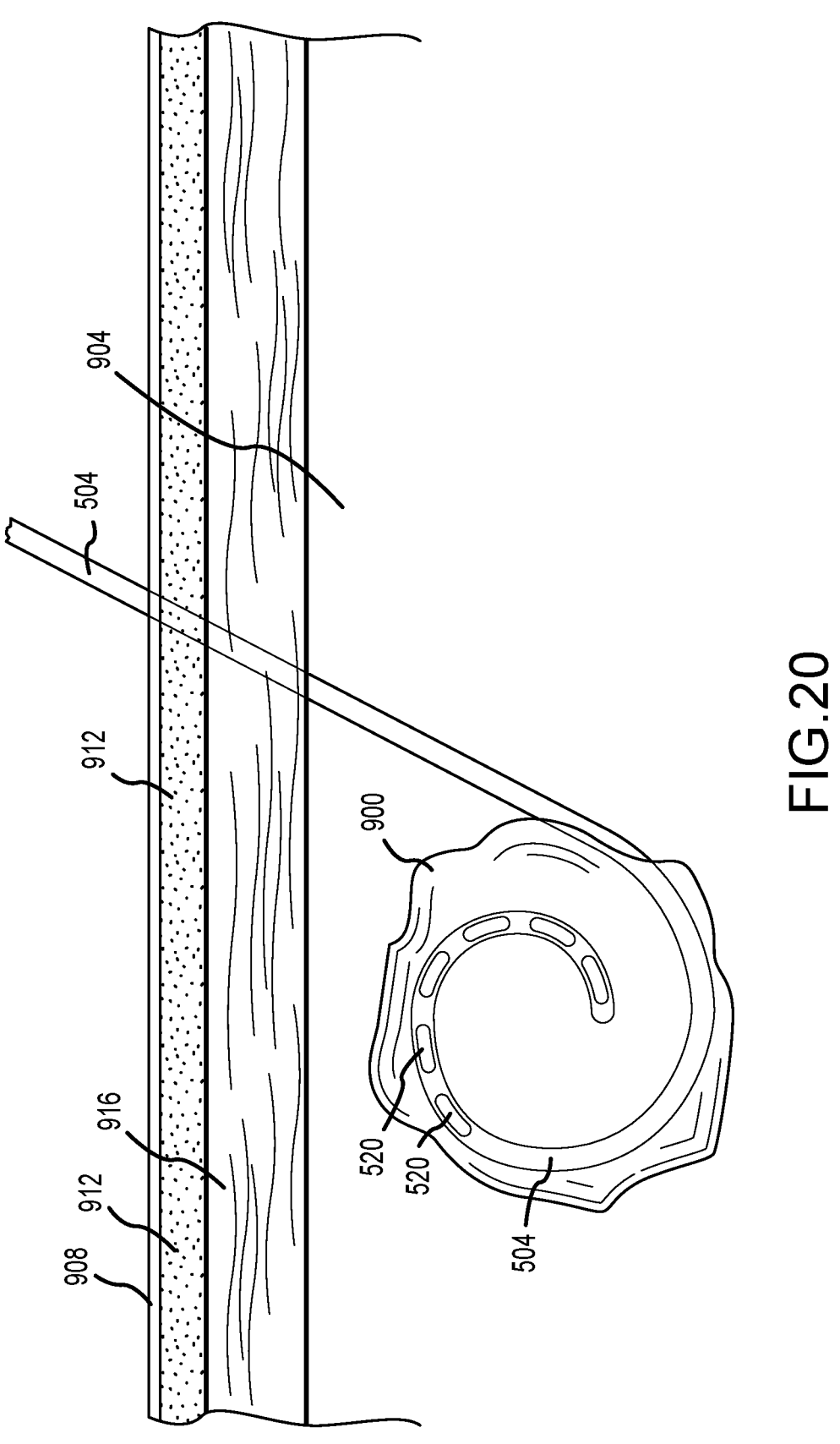
FIG. 20 shows the catheter in a locked position in the abscess according to an embodiment of the present disclosure.

In step 832, when the catheter body 504 is in the desired position within the abscess 900, the catheter body 504 is moved to a locked and coiled configuration within the abscess 900 as shown in FIG. 20.

Figure 19:
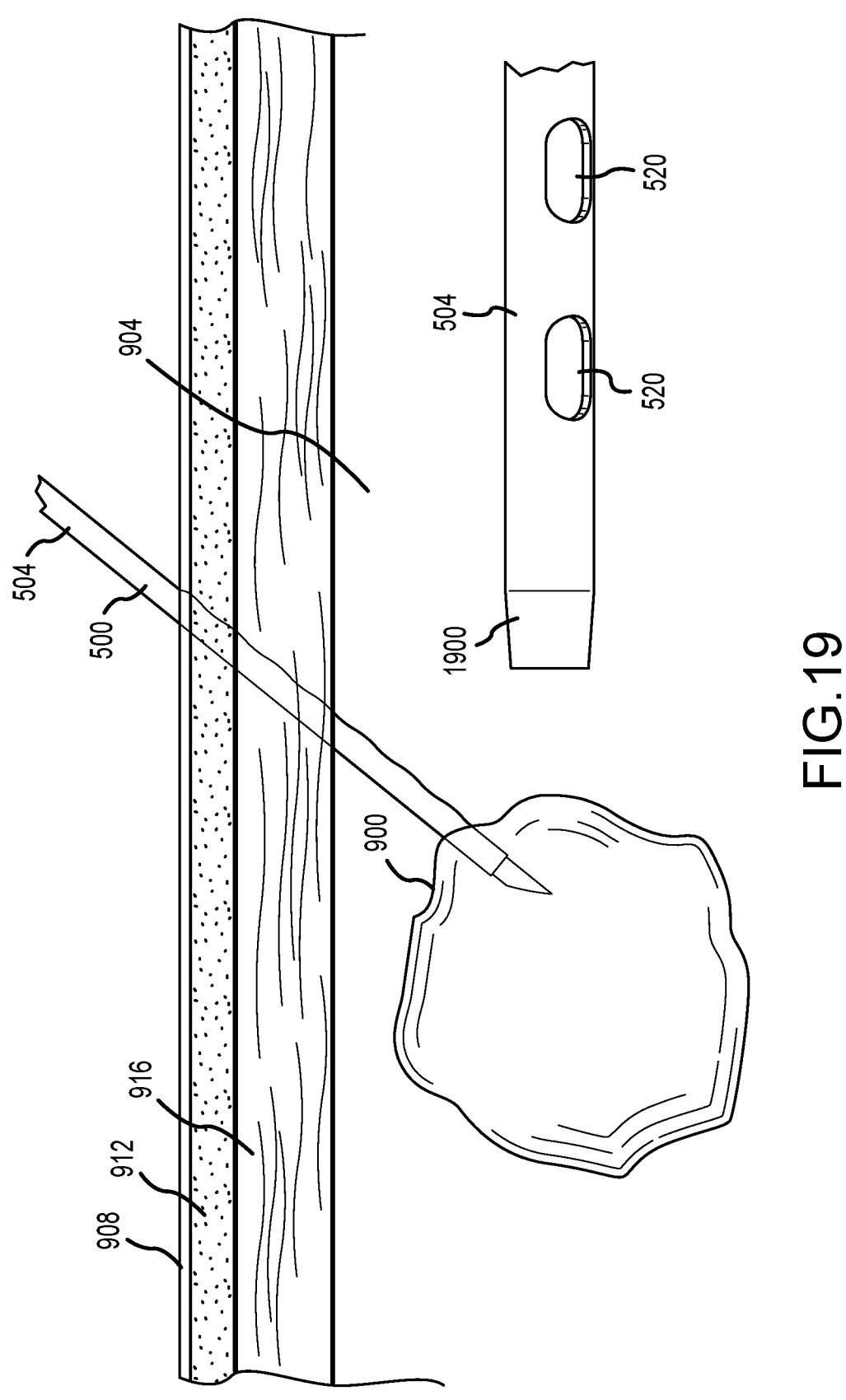
FIG. 19 shows additional detail of the catheter that is inserted into the abscess according to an embodiment of the present disclosure.

In step 836, the physician removes the outer stylet 508 from the catheter body 504 to form the second lumen along substantially the entire length of the catheter body 504. This catheter configuration is shown in FIG. 19, which shows the drainage ports 520 forming a fluid flow path through the drainage port into a hollow interior of the catheter body 504, or through the second lumen. FIG. 19 further shows the frustoconical shaped front end 1900 of the catheter body 504 reduces progressively the inner radius of the catheter body 504 that prevents the inner and outer stylets 512 and 508, respectively, from overadvancing the outer stylet 508 too far in front of the catheter body 504 when the catheter assembly 500 is advanced into the patient's body. As noted above in connection with FIG. 5, the inner stylet 512 is prevented from over advancing by the pocket 550 in a rear of the cutting tip 528. As will be appreciated, other types of inner structures can be used to restrain movement of the outer stylet beyond a predetermined position relative to the catheter body 504.

Finally, the physician, in step 840, confirms by further CT scanning that the catheter body 504 is coiled in the abscess 900 for effective drainage of abscess fluid. While the disclosure has been discussed with reference to CT scanning, it is to be understood that other imaging techniques can be used, such as ultrasound imaging, as an alternative to or as complementary to CT scanning.

Any of the steps, functions, and operations discussed herein can be performed continuously and automatically.

The exemplary systems and methods of this disclosure have been described in relation to abscess drainage. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

For example in one alternative embodiment, the slotted scalpel can be used to insert and guide other types of catheters into a patient's body, for example intravenous catheters, urinary catheters, central venous catheters, peripherally inserted central catheters, and biliary adrenal catheters.

In another alternative embodiment, the catheter assembly can be used without the slotted scalpel.

In another alternative embodiment, the slotted scalpel and/or catheter are used not only for human patients but also non-human living patients, such as in veterinary surgeries.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A scalpel, comprising:
   a cutting tip;
   a handle; and
   an elongated body joining the cutting tip and the handle, the elongated body comprising a guide channel to receive and guide a catheter along a length of the guide channel, wherein the guide channel comprises a first arcuate portion positioned between second and third arcuate portions and extending substantially an entire length of the guide channel and connected to the cutting tip, the first arcuate portion and the cutting tip comprising a metal material to reflect an X-ray spectrum of electromagnetic wave energy and each of the second and third arcuate portions comprising a polymeric non-resorbable resin to pass substantially the X-ray spectrum of electromagnetic wave energy and wherein the handle is spatially offset from a longitudinal axis of the elongated body to enable movement of the scalpel without user interference and wherein the guide channel has a semicircular cross-sectional profile perpendicular to the longitudinal axis.

2. The scalpel of claim 1, wherein the second and third arcuate portions of the guide channel extend substantially the entire length of the guide channel.

3. The scalpel of claim 1, wherein the elongated body comprises an upper arcuate surface in the guide channel and a lower arcuate surface opposing the upper arcuate surface.

4. The scalpel of claim 1, wherein a gripping surface of the handle is disposed at an angle relative to the longitudinal axis of the elongated body.

5. The scalpel of claim 1, further comprising a catheter assembly, the catheter assembly comprising a catheter body; an inner stylet within an interior passage of the catheter body and extending along a length of the catheter body; and an outer stylet within the interior passage of the catheter body and extending along the length of the catheter body, the inner and outer stylets moving independently of each other, wherein the catheter body is positioned in the guide channel.

6. The scalpel of claim 5, wherein the catheter body comprises an aspiration port and a plurality of drainage ports, wherein:
   in a first operational mode, the inner and outer stylets are positioned simultaneously in the interior passage of the catheter body and block fluid drainage through the aspiration port and plurality of drainage ports; and
   in a second operational mode, the inner stylet is removed from the catheter body while the outer stylet remains in the interior passage of the catheter body, thereby form-ing a first lumen in a volume previously occupied by the inner stylet and enabling fluid drainage from the aspiration port along the first lumen while blocking fluid drainage through the plurality of drainage ports.

7. The scalpel of claim 6 wherein:

in a third operational mode, both the inner stylets and outer stylets are removed from the interior passage of the catheter body, thereby forming a second lumen in a volume previously occupied by the inner and outer stylets and enabling fluid drainage from the aspiration port and the drainage ports along the second lumen.

8. The scalpel of claim 5, wherein the outer stylet com-prises a concave draining channel to receive and direct abscess fluid to an output of the catheter assembly.

9. The scalpel of claim 5, wherein the catheter body comprises an aspiration port and a plurality of drainage ports, the aspiration port being in a distal portion of the catheter body and the plurality of draining ports being proximal to the aspiration port, the aspiration port being positioned between a tip of the catheter and plurality of drainage ports.

10. The scalpel of claim 5, wherein a front end of the catheter body comprises a frustoconical shape that reduces progressively an interior radius of the catheter body to prevent the inner and outer stylets from advancing too far in front of the catheter body.

11. A scalpel, comprising:

a cutting tip;

a handle; and an elongated body joining the cutting tip and the handle, the elongated body comprising a guide channel to receive and guide a catheter along a length of the guide channel, wherein the guide channel comprises a first arcuate portion positioned between second and third arcuate portions and extending substantially an entire length of the guide channel and connected to the cutting tip, the first arcuate portion and the cutting tip com-prising a metal material to reflect an X-ray spectrum of electromagnetic wave energy and each of the second and third arcuate portions comprising a polymeric non-resorbable resin to pass substantially the X-ray spectrum of electromagnetic wave energy and wherein the guide channel has a semicircular cross-sectional profile perpendicular to the longitudinal axis, wherein the handle is spatially offset from a longitudinal axis of the elongated body to enable movement of the scalpel without user interference, and wherein the second and third arcuate portions of the guide channel extend along a length of the guide channel.

12. The scalpel of claim 11, wherein the elongated body comprises an upper arcuate surface in the guide channel and a lower arcuate surface opposing the upper arcuate surface and wherein a gripping surface of the handle is disposed at an angle relative to the longitudinal axis of the elongated body.

13. The scalpel of claim 11, further comprising a catheter assembly, the catheter assembly comprising a catheter body; an inner stylet within an interior passage of the catheter body and extending along a length of the catheter body; and an outer stylet within the interior passage of the catheter body and extending along the length of the catheter body, the inner and outer stylets moving independently of each other, wherein the catheter body is positioned in the guide channel.

14. The scalpel of claim 13, wherein the catheter body comprises an aspiration port and a plurality of drainage ports and wherein:

in a first operational mode, the inner and outer stylets are positioned simultaneously in the interior passage of the catheter body and block fluid drainage through the aspiration port and plurality of drainage ports; and in a second operational mode, the inner stylet is removed from the catheter body while the outer stylet remains in the interior passage of the catheter body, thereby form-ing a first lumen in a volume previously occupied by the inner stylet and enabling fluid drainage from the aspiration port along the first lumen while blocking fluid drainage through the plurality of drainage ports.

15. The scalpel of claim 14 wherein:

in a third operational mode, both the inner stylets and outer stylets are removed from the interior passage of the catheter body, thereby forming a second lumen in a volume previously occupied by the inner and outer stylets and enabling fluid drainage from the aspiration port and the drainage ports along the second lumen.

16. The scalpel of claim 13, wherein the outer stylet comprises a concave draining channel to receive and direct abscess fluid to an output of the catheter assembly.

17. The scalpel of claim 13, wherein the catheter body comprises an aspiration port and a plurality of drainage ports, the aspiration port being in a distal portion of the catheter body and the plurality of draining ports being proximal to the aspiration port, the aspiration port being positioned between a tip of the catheter and plurality of drainage ports.

18. The scalpel of claim 13, wherein a front end of the catheter body comprises a frustoconical shape that reduces progressively an interior radius of the catheter body to prevent the inner and outer stylets from advancing too far in front of the catheter body.

* * * * *